(12) United States Patent
Watanabe

(10) Patent No.: US 11,701,042 B2
(45) Date of Patent: Jul. 18, 2023

(54) SIGNAL PROCESSING APPARATUS AND SIGNAL PROCESSING METHOD

(71) Applicant: Taishi Watanabe, Tokyo (JP)

(72) Inventor: Taishi Watanabe, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 444 days.

(21) Appl. No.: 16/804,254

(22) Filed: Feb. 28, 2020

(65) Prior Publication Data

US 2020/0289004 A1   Sep. 17, 2020

(30) Foreign Application Priority Data

Mar. 14, 2019 (JP) .................................. 2019-047671
May 31, 2019 (JP) .................................. 2019-103117

(51) Int. Cl.
*A61B 5/242* (2021.01)
*A61B 5/00* (2006.01)
(Continued)

(52) U.S. Cl.
CPC ............ *A61B 5/242* (2021.01); *A61B 5/4041* (2013.01); *A61B 2562/0223* (2013.01); *A61N 1/0456* (2013.01); *A61N 1/36014* (2013.01)

(58) Field of Classification Search
CPC .................. A61B 5/242; A61B 5/4041; A61B 2562/0223; A61B 5/721
See application file for complete search history.

(56) References Cited

U.S. PATENT DOCUMENTS 10,307,105 B2   6/2019   Taulu et al.
10,433,758 B2   10/2019  Kawabata
(Continued)

FOREIGN PATENT DOCUMENTS

JP   2011-67497    4/2011
JP   2016-221092   12/2016
(Continued)

OTHER PUBLICATIONS

K. Sekihara et al., "Sensor array outputs and spatial filters", "Adaptive Spatial Filters for Electromagnetic Brain Imaging", Springer, Germany, 2008, pp. 9-25.
K. Sekihara et al., "Dual signal subspace projection (DSSP): A novel algorithm for removing large interference in biomagnetic measurements", J. Neural Eng., Jun. 2016.
(Continued)

*Primary Examiner* — Amanda K Hulbert
*Assistant Examiner* — Philip C Edwards
(74) *Attorney, Agent, or Firm* — IPUSA, PLLC

(57) ABSTRACT

A signal processing apparatus includes a memory, and a processor coupled to the memory and configured to perform a process including obtaining measurement data including a signal of interest and an interference signal generated in proximity to a signal source of the signal of interest, estimating a signal source in an extraction target area including the signal source of the signal of interest and a signal source of the interference signal based on the measurement data, selecting the signal source of the interference signal based on a result of the estimating a signal source and extracting interference signal data generated from the selected signal source of the interference signal, and extracting the signal of interest by removing a common part between the measurement data and the interference signal data.

15 Claims, 20 Drawing Sheets

(51) Int. Cl.
*A61N 1/04* (2006.01)
*A61N 1/36* (2006.01)

(56) References Cited

U.S. PATENT DOCUMENTS

| | | | |
|---|---|---|---|
| 2016/0338608 A1* | 11/2016 | Nagasaka | A61B 5/243 |
| 2018/0014738 A1* | 1/2018 | Tanaka | A61B 5/0265 |
| 2018/0146926 A1 | 5/2018 | Ishikawa | |
| 2018/0333062 A1 | 11/2018 | Watanabe | |

FOREIGN PATENT DOCUMENTS

| | | |
|---|---|---|
| JP | 2018-192236 | 12/2018 |
| WO | 2013/111072 | 8/2013 |
| WO | 2016/175020 | 11/2016 |

OTHER PUBLICATIONS

T. Watanabe et al., "Removal of Stimulus-Induced Artifacts in Functional Spinal Cord Imaging", 35th Annual International Conference of the IEEE EMBS, Jul. 2013, pp. 3391-3394.
M. A. Uusitalo et al., "Signal-space projection method for separating MEG or EEG into components", Medical & Biological Engineering & Computing, Mar. 1997, pp. 135-140.
K. Sekihara et al., "Adaptive Beamformers", "Electromagnetic Brain Imaging: A Bayesian Perspective", Springer International Publishing, Switzerland, 2015, pp. 46-49.
Y. Adachi et al., "Reduction of Non-periodic Environmental Magnetic Noise in MEG Measurement by Continuously Adjusted Least Squares Method", IEEE Transactions on Applied Superconductivity, Mar. 2001, vol. 11, No. 1, pp. 669-672.
Japanese Office Action for 2019-103117 dated Dec. 13, 2022.

\* cited by examiner

SIGNAL PROCESSING APPARATUS AND SIGNAL PROCESSING METHOD

CROSS-REFERENCE TO RELATED APPLICATION

The present application is based on and claims priority under 35 U.S.C. § 119 to Japanese Patent Application No. 2019-047671, filed on Mar. 14, 2019, and Japanese Patent Application No. 2019-103117, filed on May 31, 2019, the contents of which are incorporated herein by reference in their entirety.

BACKGROUND OF THE INVENTION

1. Field of the Invention

The present invention relates to a signal processing apparatus and a signal processing method.

2. Description of the Related Art

For example, as a measurement method of a biomagnetic field, a measurement method in which stimulation is given to a part of a subject to induce a nerve activity at a part to be measured, and a magnetic field emitted from the nerve activity is measured by a sensor, has been known. In such a measurement method, an interference magnetic field is induced by, for example, the stimulation or a movement of muscles caused by the stimulation, and the interference magnetic field becomes noise.

Thus, a method in which a signal of interest that does not include interference magnetic field data is obtained by eliminating a component of measurement data that includes the interference magnetic field data and that does not include magnetic field data of interest from a component of measurement data that includes the interference magnetic field data, is proposed. In this method, first, measurement data including the interference magnetic field data is obtained by giving the stimulation in a state in which a part to be measured is close to a magnetic field measuring apparatus, and measurement data that does not include magnetic field data of interest is obtained in a state in which the part to be measured is away from the magnetic field measuring apparatus. Subsequently, the signal of interest is obtained by eliminating a component of the second obtained measurement data from a component of the first obtained measurement data (Patent Document 1).

A method in which a body motion noise is removed from a pulse wave signal by inputting a body motion signal filtered by a transfer function derived by modeling an influence of a body movement on a blood flow to an adaptive filter and decreasing an output signal of the adaptive filter from the pulse wave signal, is proposed (Patent Document 2).

Patent Document 1: Japanese Unexamined Patent Application Publication No. 2018-192236
Patent Document 2: Japanese Unexamined Patent Application Publication No. 2016-221092
Patent Document 3: WO 2016/175020
Non Patent Document 1: K. Sekihara, S. S. Nagarajan, Adaptive Spatial Filters for Electromagnetic Brain Imaging, Springer, 2008
Non Patent Document 2: K. Sekihara, et al., Dual signal subspace projection (DSSP): A novel algorithm for removing large interference in biomagnetic measurements, J. Neural Eng., 13, 036007, 2016
Non Patent Document 3: T. Watanabe, et al., Removal of Stimulus-Induced Artifacts in Functional Spinal Cord Imaging, 35th Annual International Conference of the IEEE EMBS, 2013
Non Patent Document 4: M. A. Uusitalo, R. J. Ilmoniemi, Signal-space projection method for separating MEG or EEG into components, Medical & Biological Engineering & Computing 135-140, 1997
Non Patent Document 5: Sekihara K, Nagarajan S. S., Electromagnetic Brain Imaging: A Bayesian Perspective, Springer International Publishing, 2015

SUMMARY OF THE INVENTION

According to one aspect of the present invention, a signal processing apparatus includes a memory, and a processor coupled to the memory and configured to perform a process including obtaining measurement data including a signal of interest and an interference signal generated in proximity to a signal source of the signal of interest, estimating a signal source in an extraction target area including the signal source of the signal of interest and a signal source of the interference signal based on the measurement data, selecting the signal source of the interference signal based on a result of the estimating a signal source and extracting interference signal data generated from the selected signal source of the interference signal, and extracting the signal of interest by removing a common part between the measurement data and the interference signal data.

DETAILED DESCRIPTION OF THE PREFERRED EMBODIMENTS

When the magnetic field data of interest is obtained by removing the interference magnetic field data based on two pieces of the measurement data, there is a problem that inspection time becomes long because measurement is required to be performed twice. Additionally, when a signal source of the interference magnetic field is near or within a measurement area of the magnetic field data, there is a possibility that a magnetic field component to be measured and an interference magnetic field component, which are included in the measurement data, cannot be distinguished. From this, when the interference magnetic field data cannot be removed from the measurement data, a valid magnetic field data of interest cannot be obtained.

It is a general object of the present invention to extract the magnetic field data of interest by removing the interference magnetic field data from the measurement data of the magnetic field and shorten the measurement time.

In the following, embodiments will be described with reference to the drawings.

First Embodiment

Figure 1A:
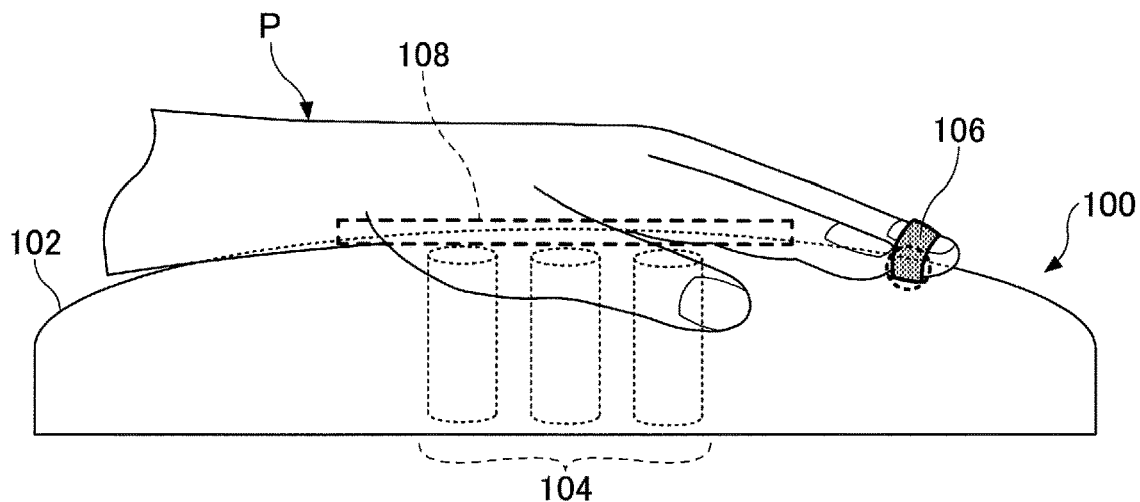
FIG. 1A and FIG. 1B are drawings illustrating a main part of a biomagnetic field measuring apparatus including a signal processing apparatus according to a first embodiment.
Figure 1B:
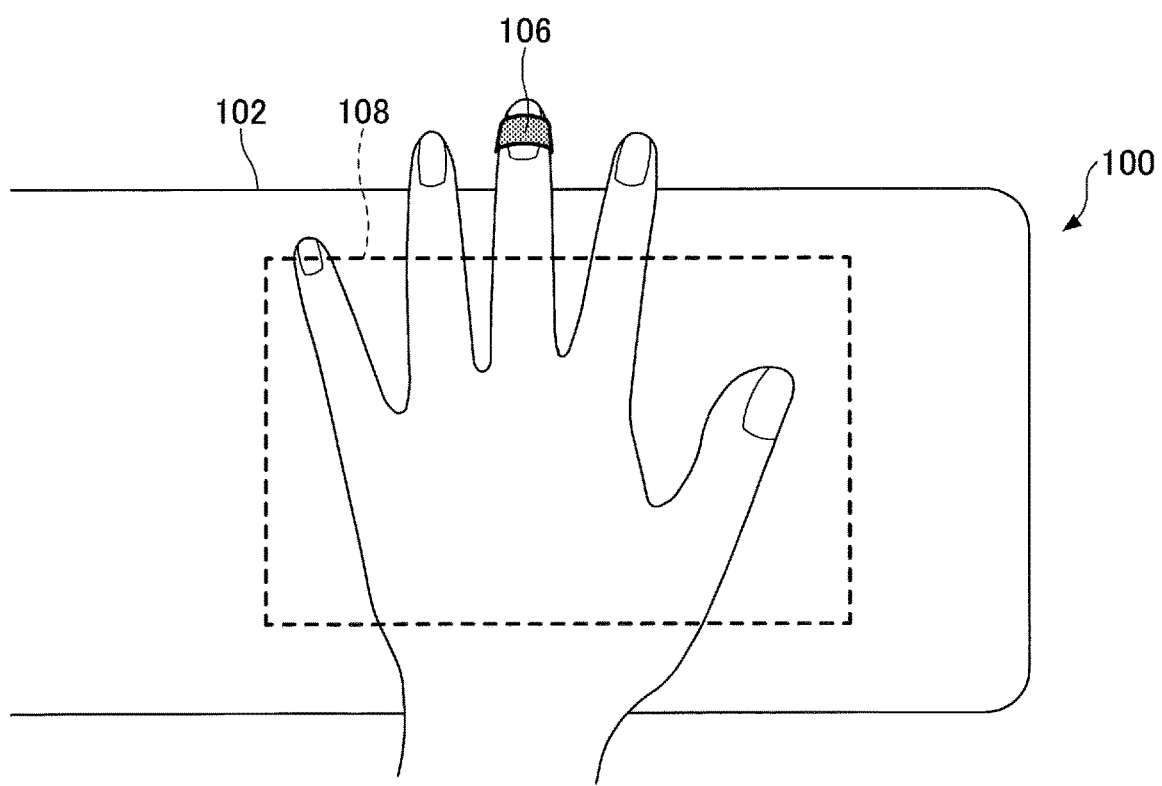
Figure 2:
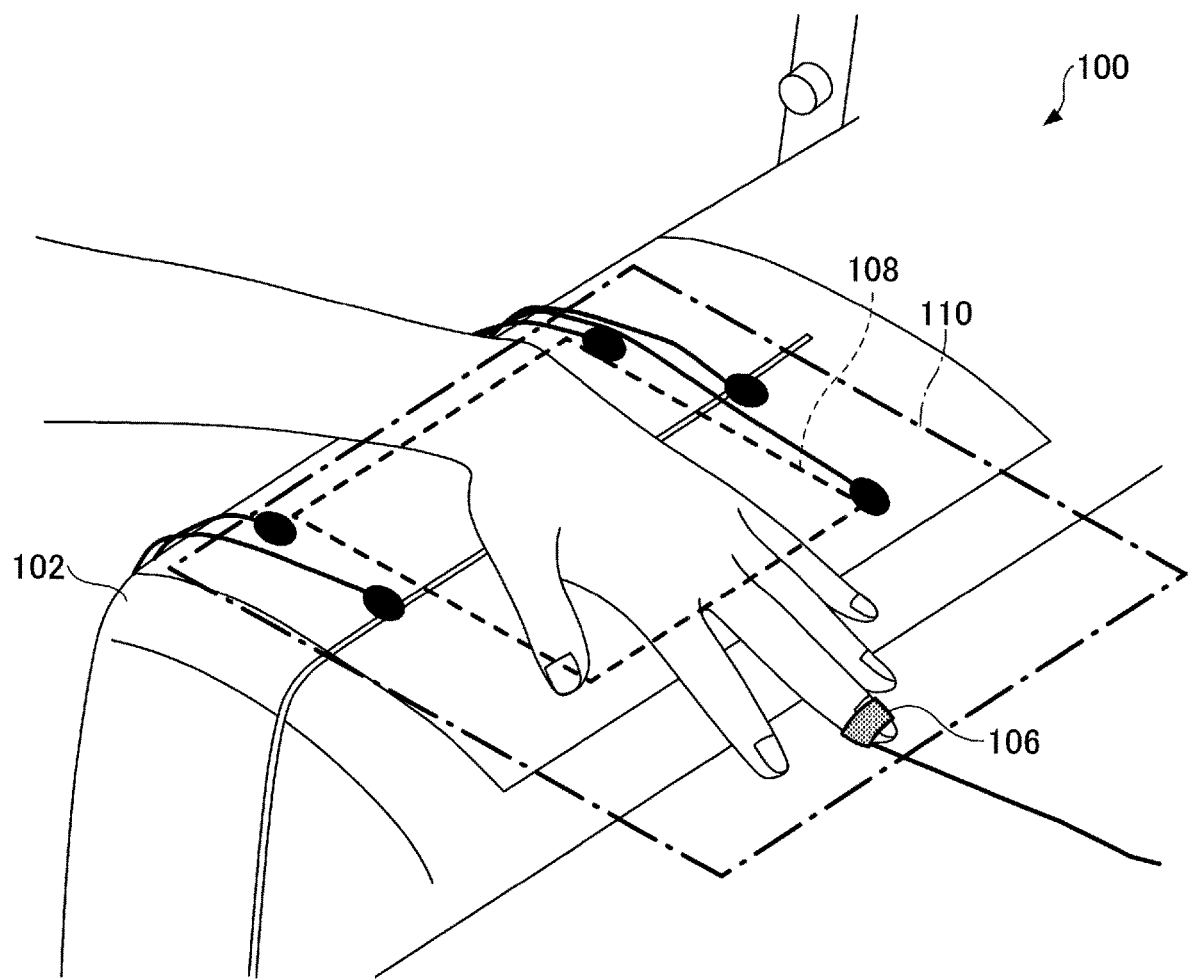
FIG. 2 is a drawing illustrating a scene of measuring a magnetic field generated from a subject by the biomagnetic field measuring apparatus.

FIG. 1A and FIG. 1B are drawings illustrating a main part of a biomagnetic field measuring apparatus including a signal processing apparatus 10 (which is illustrated in FIG. 2) according to a first embodiment.

A biomagnetic field measuring apparatus 100 includes a base 102 including a contact part with a subject P, a magnetic field detector 104 disposed inside the base 102, and a nerve stimulation device, which is not illustrated, coupled to an electrode 106. The magnetic field detector 104 is one example of a measurement executing unit. The nerve stimulation device applies electrical stimulation to the subject P through the electrode 106 in accordance with a predetermined stimulation condition. In FIG. 1, the electrode 106 is hidden by a band for an attachment to the subject P.

The magnetic field detector 104 includes a sensor array including multiple sensors that detect a magnetic field and a driving circuit that drives the sensor array. In FIG. 1A and FIG. 1B, only the sensor array is illustrated. The magnetic field detector 104 measures a magnetic field that is caused by the electrical stimulation applied to the subject P and that is created by an electrical signal in the human body indicating a nerve operation of a body part of the subject P to be measured.

The biomagnetic field measuring apparatus 100 measures a magnetic field generated by nerve activity of the body part of the subject P to be measured, by the sensor array, in a state in which the subject P (e.g., a palm) is in contact with a measurement area 108 where a magnetic field can be measured by the magnetic field detector 104, and the stimulation is given to the subject P from the electrode. Here, in FIG. 1A and FIG. 1B, the palm of the subject P is a body part to be measured, electrical stimulation is given by contacting the electrode giving the stimulation to a fingertip (e.g., a part in proximity to a first joint of a middle finger), and a nerve-induced magnetic field generated by nerve activity of the palm induced by the electrical stimulation is obtained by the sensor array.

In this case, the electrode 106 contacting the middle finger and an electric cable (which is not illustrated) coupled to the electrode are signal sources of an interference signal (i.e. an interference magnetic field). For example, the interference signal is noise (i.e., a stimulation artifact) generated by other parts than the subject P to be measured in response to the stimulation. However, since the electric cable is generally located away from a magnetic sensor compared with the electrode 106, the interference signal obtained by the magnetic field detector 104 is mainly generated from the electrode 106. Therefore, the following description assumes that the interference signal is generated from the electrode 106.

The stimulation given to the subject P may be other than an electric current, and for example, the stimulation may be magnetically given to the body part to be measured. Additionally, the electrical stimulation may be given to both the middle finger and a forefinger by contacting the electrode to each of the middle finger and the forefinger.

FIG. 2 is a drawing illustrating a scene of measuring a magnetic field generated from the subject P by the biomagnetic field measuring apparatus 100. On the base 102, the palm of the subject P is placed on the measurement area 108 facing the sensor array disposed in the base 102. In an example illustrated in FIG. 2, the electrode 106 that gives the stimulation to the subject P and that is a signal source of the interference signal is located outside of the measurement area 108.

Figure 3:
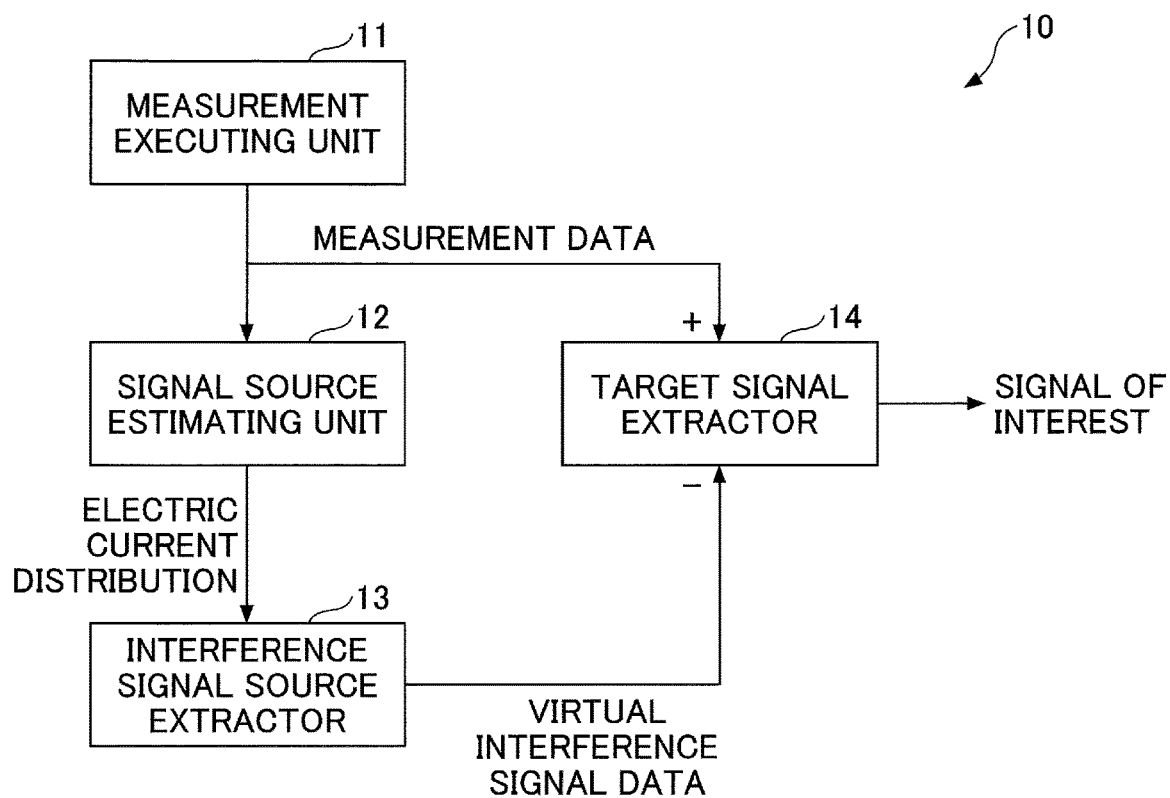
FIG. 3 is a block diagram illustrating an example of the signal processing apparatus according to the first embodiment.

An extraction target area 110 is an area including a position of the palm that is a signal source of a signal of interest and a position of the electrode 106 that is a signal source of the interference signal, and is predetermined by the magnetic field detector 104 before measuring a magnetic field. As described later, the signal processing apparatus 10 of the embodiment (which is illustrated in FIG. 3) estimates electric current distribution in the extraction target area 110 and extracts the magnetic field data that is generated from a signal source of the interference signal and that is detected by the sensor array (i.e., interference signal data) by computation. The signal processing apparatus 10 extracts the signal of interest emitted from the palm that is the body part of the object to be measured by removing a common part between the measurement data obtained by the magnetic field detector 104 and the interference signal data.

Here, in FIG. 2, the palm of the subject is an object to be measured, but any body part of the subject may be an object to be measured. Additionally, the subject is not limited to a human and may be an animal such as an anthropoid ape.

FIG. 3 is a block diagram illustrating an example of the signal processing apparatus 10 according to the first embodiment. FIG. 3 also illustrates a functional block of the signal processing apparatus 10. As described above, the signal processing apparatus 10 is included in the biomagnetic field measuring apparatus 100, and processes the magnetic field data obtained by the biomagnetic field measuring apparatus 100. The signal processing apparatus 10 includes a measurement executing unit 11, a signal source estimating unit 12, an interference signal source extractor 13, and a target signal extractor 14.

For example, the measurement executing unit 11 is achieved by the magnetic field detector 104 (i.e., the sensor array) illustrated in FIG. 2 and a control function of the magnetic field detector 104 operated by a signal processing program executed by a controller such as a central processing unit (CPU) included in the signal processing apparatus 10. Here, the control function of the magnetic field detector 104 in the measurement executing unit 11 may be implemented by, for example, a logic circuit such as a field programmable gate array (FPGA).

The measurement executing unit 11 obtains the measurement data including magnetic field information emitted from the body part of the object to be measured in a state in which the body part of the subject P to be measured is closely contacted to the sensor array. The measurement data includes a signal of interest indicating a magnetic field desired to be measured, emitted from the body part of the object to be measured, and the interference signal occurring in proximity to the sensor array at the signal source of the signal of interest. The measurement data obtained by the measurement executing unit 11 may be temporarily stored in a memory in the signal processing apparatus 10 since the measurement data is used in subsequent processing of the target signal extractor 14.

For example, the interference signal is generated by a magnetic field caused by the electrical stimulation given to the subject P, and is generated from the electrode 106 attached to the subject P to give the electrical stimulation and from body tissue in proximity to the electrode 106. Thus, the following description assumes that the signal source of the interference signal is the electrode 106.

For example, the measurement executing unit 11 can obtain measurement data $B_s$ in accordance with a model expressed in Eq. (1).

$$B_s = A + B + \varepsilon \quad (1)$$

In Eq. (1), A indicates an interference signal component, B indicates a component of the signal of interest, and $\varepsilon$ indicates white noise.

For example, functions of the signal source estimating unit 12, the interference signal source extractor 13, and the target signal extractor 14 are implemented by the signal processing program executed by the controller such as the CPU included in the signal processing apparatus 10. The functions of the signal source estimating unit 12, the interference signal source extractor 13, and the target signal extractor 14 may be implemented by, for example, the logic circuit such as the FPGA.

The signal source estimating unit 12 estimates a signal source generating a magnetic field in the extraction target area 110 including the sensor array at the signal source of the signal of interest and the electrode 106 that is the signal source of the interference signal. When the signal source estimating unit 12 estimates the signal source, the extraction target area 110, which includes both a position of the signal source of the signal of interest and a position of the signal source of the interference signal, is set first. The signal source estimating unit 12 estimates the distribution of the electric current in a plane of the extraction target area 110 using an estimation algorithm such as a spatial filter method (Non-Patent Document 1).

When the signal source of the interference signal is away from the signal source of the signal of interest and it is difficult to set the extraction target area 110 including the signal source of the interference signal from a position relationship with the sensor array, the extraction target area 110 including only the signal source of the signal of interest may be set. However, in this case, it is preferable to expand the extraction target area 110 toward the position of the signal source of the interference signal. Additionally, for example, the extraction target area 110 may be set to include the position of the signal source of the interference signal based on form information indicating the position of the signal source of the sensor array and the position of the signal source of the interference signal using a method of Patent Document 3.

For example, the interference signal source extractor 13 selects an area having characteristics of the interference signal from among signal sources estimated by the signal source estimating unit 12 as the signal source of the interference signal. For detecting the position of the signal source of the interference signal, the form information indicating the position of the signal source of the interference signal may be used.

The signal source of the interference signal may be selected automatically using previously recognized position information of the signal source of the interference signal. Alternatively, the signal source of the interference signal may be selected by displaying, for example, an electric current map by which electric current distribution is visually recognized on a display device and causing an operator of the biomagnetic field measuring apparatus 100 to input a position of the signal source of the interference signal.

The interference signal source extractor 13 extracts interference signal data (i.e., an electric current component) generated from the selected signal source of the interference signal. For example, the interference signal data is extracted by obtaining temporal transition of the electric current of the signal source of the interference signal based on the electric current distribution. In the measurement of the biomagnetic field, a relation between change in the electric current component of a virtual interference signal and change in the magnetic field component generated from the selected signal source is considered to be a linear relation. Therefore, for example, the interference signal source extractor 13 generates the virtual interference signal data (i.e., the magnetic field component) by processing such as multiplying the extracted interference signal data (i.e., the electric current component) by a predetermined coefficient, and outputs the generated virtual interference signal data to the target signal extractor 14. Here, the virtual interference signal data (i.e., the magnetic field component) is a predicted value of the magnetic field data generated by the signal source of the interference signal.

The virtual interference signal data (i.e., the magnetic field component) $B_a$ generated by the interference signal source extractor 13 is considered to conform to Eq. (2).

$$B_a = A + C + \varepsilon \quad (2)$$

In Eq. (2), A indicates the interference signal component, C indicates a signal component having distribution different from the signal of interest, and ε indicates white noise. Eq. (2) is similar to Eq. (1) except that Eq. (2) does not have the signal component B of interest in Eq. (1), but instead, Eq. (2) has the signal component C with distribution different from the signal of interest.

The target signal extractor 14 extracts the signal of interest by removing a common part between the measured data obtained by the measurement executing unit 11 and the virtual interference signal data. A symbol "+" illustrated over the target signal extractor 14 in FIG. 3 and a symbol "−" illustrated under the target signal extractor 14 represent a concept of extracting the signal of interest by subtracting the component of the virtual interference signal data from the component of the measured data.

For example, a method according to Non-Patent Document 3 is used for removing the common part between the measured data and the virtual interference signal data. This can extract the signal component of interest generated by removing the interference signal component from the measured data, by one measurement of the body part of the subject P to be measured.

Figure 4:
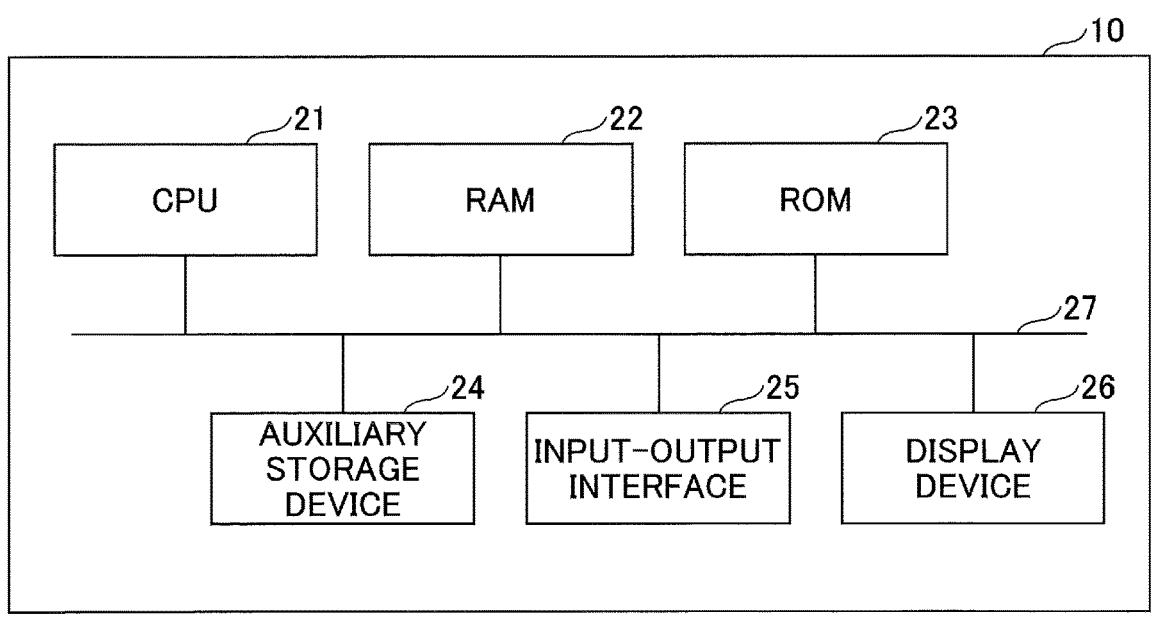
FIG. 4 is a drawing illustrating an example of a hardware configuration of the signal processing apparatus of FIG. 3.

FIG. 4 is a drawing illustrating an example of a hardware configuration of the signal processing apparatus 10 of FIG. 3. The signal processing apparatus 10 is, for example, an information processing device. The information processing device includes a CPU 21, a RAM 22, a ROM 23, an auxiliary storage device 24, an input-output interface 25, and a display device 26, and these are mutually connected by a bus 27.

The CPU 21 controls an overall operation of the signal processing apparatus 10. The CPU 21 achieves various functions illustrated in FIG. 3 by executing the signal processing program stored in the ROM 23 or the auxiliary storage device 24. The CPU 21 may control an overall operation of the biomagnetic field measuring apparatus 100.

The RAM 22 is used as a work area of the CPU 21 and may include a non-volatile RAM for storing the signal processing program and information. The ROM 23 stores, for example, various programs and parameters used in the various programs. The signal processing program of the embodiment may be stored in ROM 23.

The auxiliary storage device 24 is a storage device such as a solid state drive (SSD) and a hard disk drive (HDD), and stores, for example, a control program such as an operating system (OS) for controlling an operation of the signal processing apparatus 10 and various data and files required for the operation of the signal processing apparatus 10.

The input-output interface 25 includes, for example, a user interface such as a touch panel, a keyboard, an operation button, and a speaker, and a communication interface for communicating with other electronic devices. The display device 26 displays, for example, an operation window for causing the measurement executing unit 11 to execute measurement, and a waveform indicating the measurement data obtained by the measurement executing unit 11.

Figure 5:
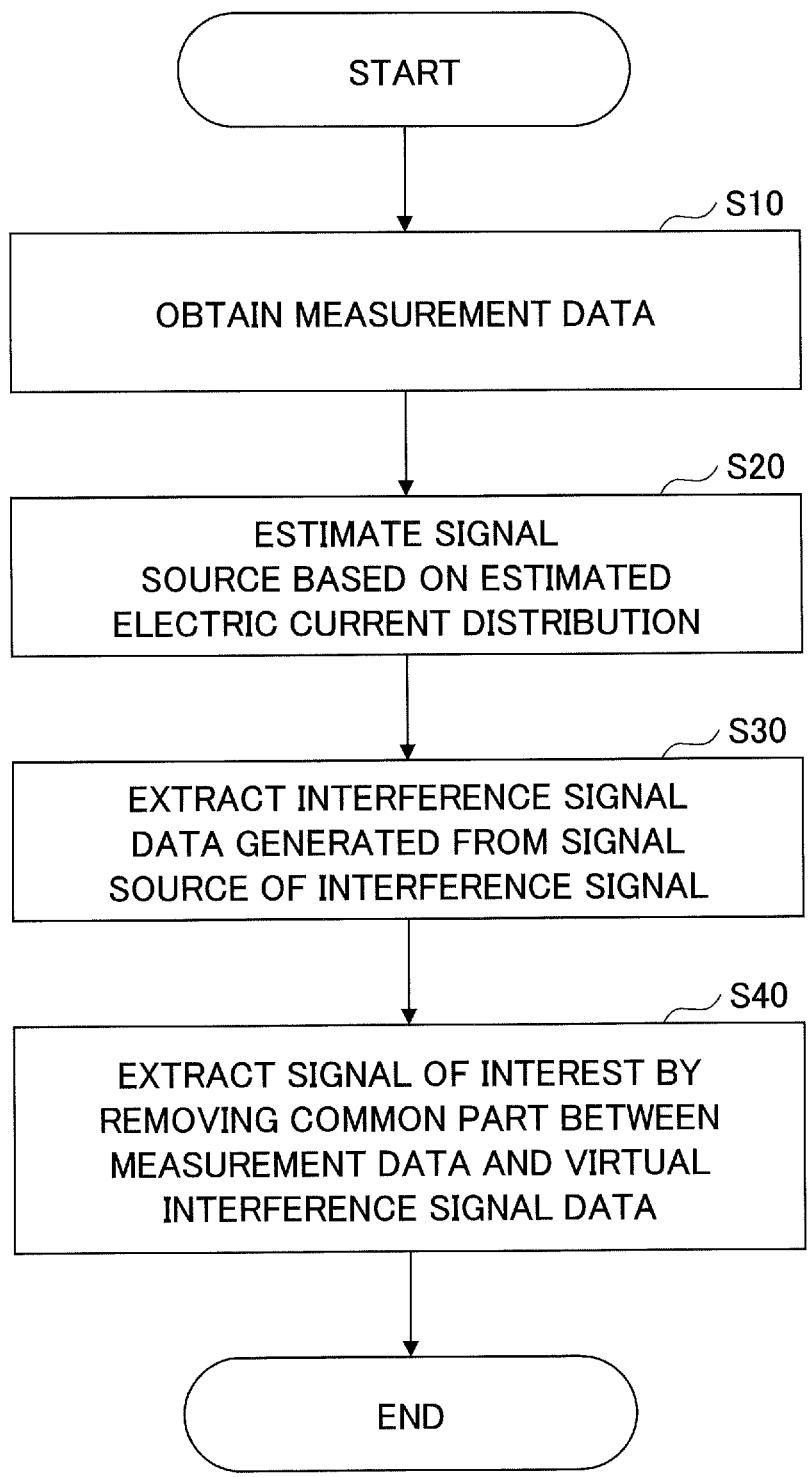
FIG. 5 is a flowchart illustrating an example of an operation of the signal processing apparatus of FIG. 3.

FIG. 5 is a flowchart illustrating an example of an operation of the signal processing apparatus 10 of FIG. 3. That is, FIG. 5 illustrates an example of a signal processing method by the signal processing apparatus 10 and a signal processing program that causes the signal processing apparatus 10 to perform signal processing.

First, in step S10, the measurement executing unit 11 obtains the measurement data including the magnetic field information emitted from the body part to be measured. Next, in step S20, the signal source estimating unit 12 estimates a signal source that generates a magnetic field in the extraction target area 110 illustrated in FIG. 2 to obtain the electric current distribution.

Next, in step S30, the interference signal source extractor 13 extracts the signal source in the area considered to be a generation source of the interference signal from among the signal sources estimated in step S20 as the interference signal data (i.e., the electric current component). The interference signal source extractor 13 generates the virtual interference signal data (i.e., the magnetic field component) based on the extracted interference signal data (i.e., the electric current component).

Next, in step S40, the target signal extractor 14 extracts the signal of interest by removing a common part between the measurement data obtained by the measurement executing unit 11 and the virtual interference signal data. Consequently, the process of removing the virtual interference signal data from the measurement data to generate the signal of interest ends.

Figure 6:
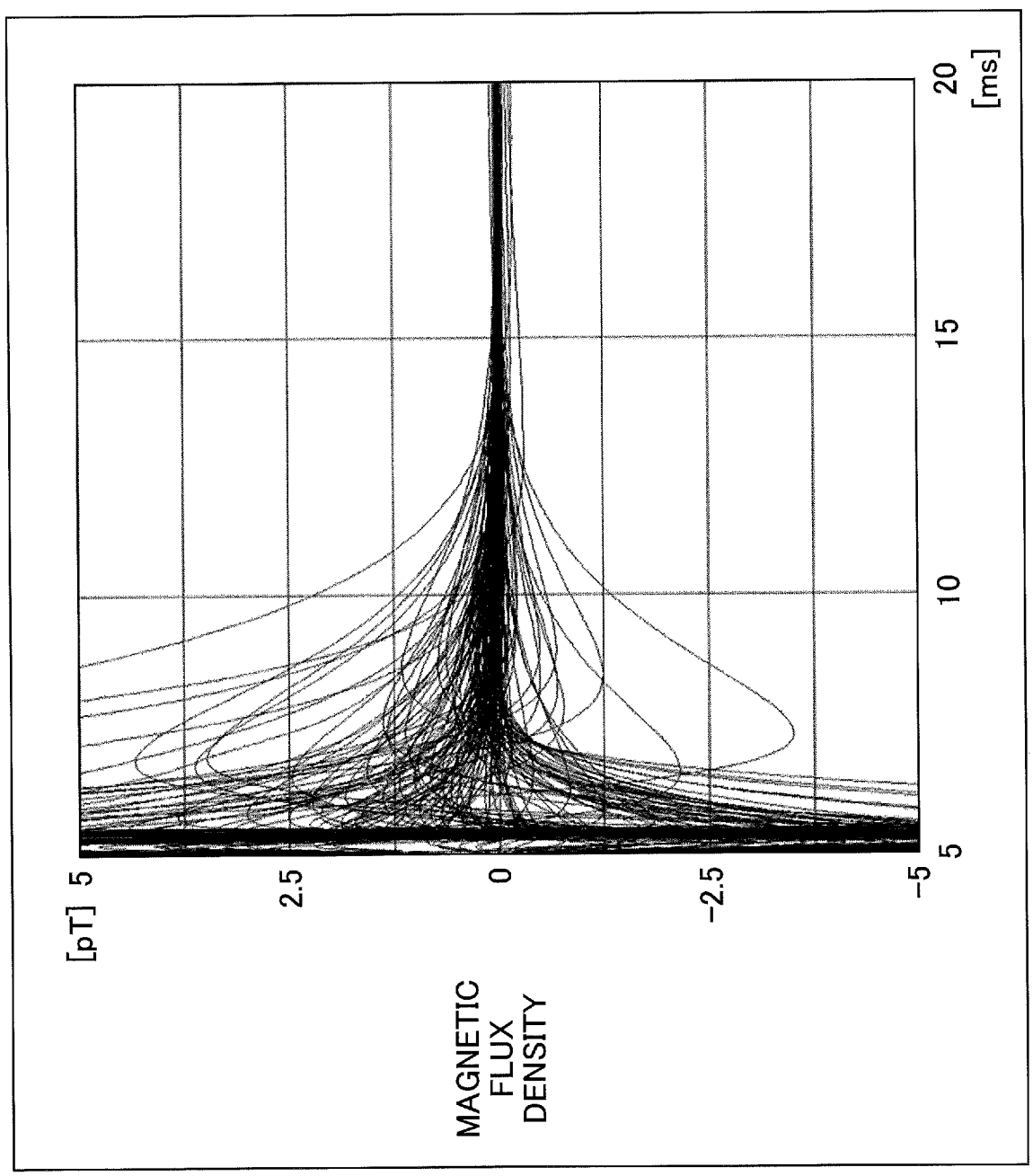
FIG. 6 is a drawing illustrating an example of measurement data obtained by measurement by the measurement executing unit of FIG. 3.

FIG. 6 is a drawing illustrating an example of the measurement data obtained by measurement by the measurement executing unit 11 of FIG. 3. FIG. 6 illustrates an example of temporal changes in the magnetic flux density, which is an output value of each sensor of the sensor array (which is raw data); in this example, the electrical stimulation is applied 5 ms after starting the measurement. FIG. 6 illustrates the measurement data after the electrical stimulation is applied.

As illustrated in FIG. 2, the sensor array (i.e., the measurement area 108) and the electrode 106 that is a part applying the stimulation, are only a few centimeters away. In FIG. 6, from the position of a hand and the conduction velocity of the induced nerve activity, it is considered that a magnetic field waveform emitted by the electric current generated by the nerve activity exists in around 6 ms to 10 ms. However, the magnetic field waveform caused by the nerve activity is buried in artificial noise (i.e., artifact noise) generated by the electrical stimulation, and the magnetic field waveform caused by the nerve activity cannot be observed in FIG. 6.

Figure 7:
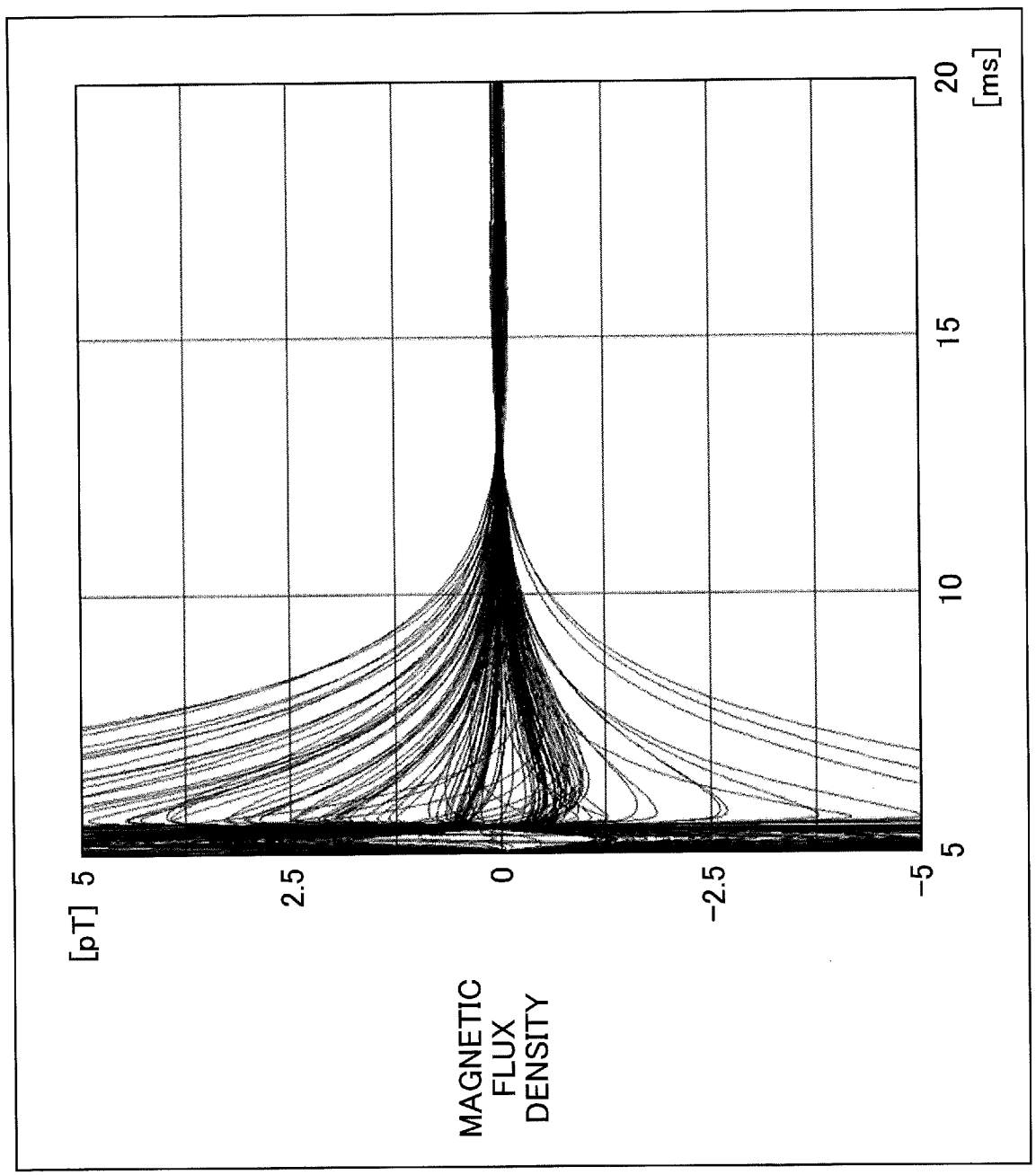
FIG. 7 is a drawing illustrating an example of interference signal data (a magnetic field component) generated by the interference signal source extractor of FIG. 3.

FIG. 7 is a drawing illustrating an example of the interference signal data (i.e., the magnetic field component) generated by the interference signal source extractor 13 of FIG. 3. FIG. 7 has the same scale as FIG. 6. The interference signal data illustrated in FIG. 7 is included in the measurement data illustrated in FIG. 6, and it can be observed that the artifact noise generated from the electrode 106 by the electrical stimulation is considerably large.

Figure 8:
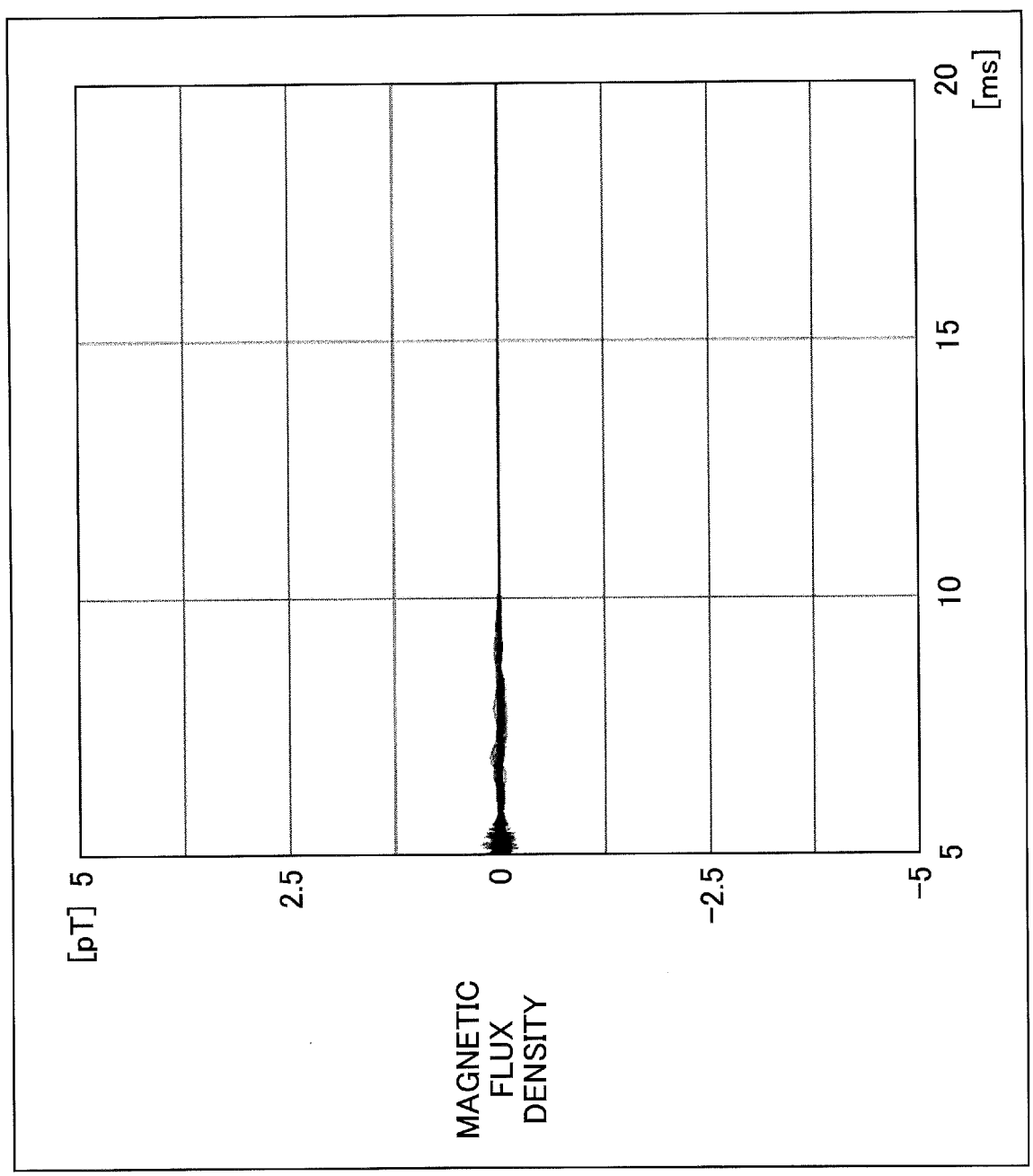
FIG. 8 is a drawing illustrating an example of a signal of interest extracted by the target signal extractor of FIG. 3.
Figure 9:
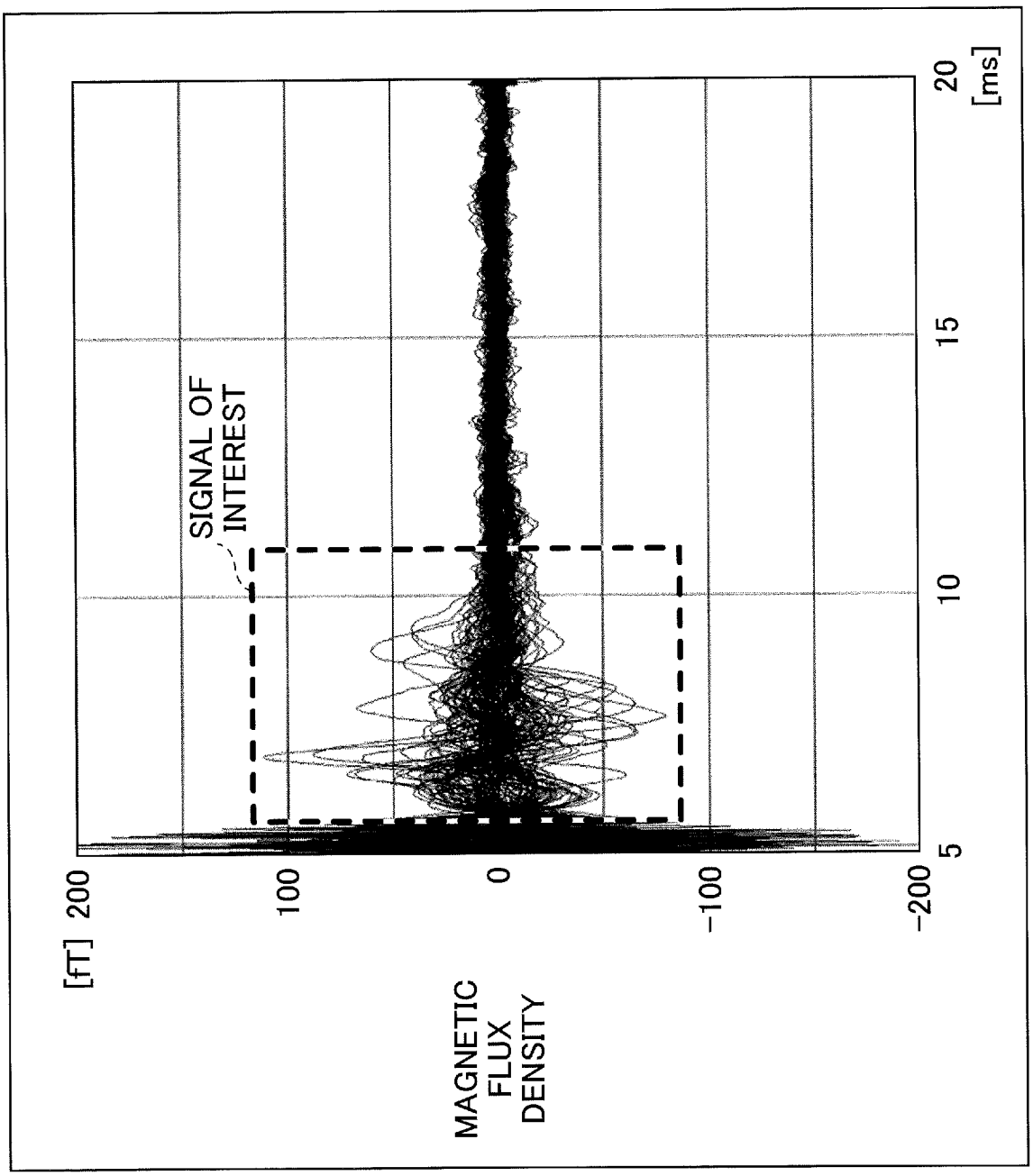
FIG. 9 is an enlarged view of the main part of FIG. 8.

FIG. 8 and FIG. 9 are drawings illustrating an example of a signal of interest extracted by the target signal extractor 14 of FIG. 3. That is, FIG. 8 and FIG. 9 illustrate changes in the magnetic field of the signal of interest generated by removing a common part between the measurement data (FIG. 6) obtained by the magnetic field detector 104 and the interference signal data (FIG. 7) generated by the interference signal source extractor 13. FIG. 8 has the same scale as FIG. 6 and FIG. 7. FIG. 9 is an enlarged view of the main part of FIG. 8, and the scale of the magnetic flux density (i.e., a vertical axis) is multiplied by 1000 compared with FIG. 8.

As seen in FIG. 8 and FIG. 9, the process of the signal processing apparatus 10 can extract the signal of interest buried in the measurement data by the interference signal data using the measurement data obtained in one measurement. That is, the signal of interest can be extracted by predicting the interference signal data (i.e., the magnetic field component) detected by the sensor array based on the prediction of the electric current component at the signal source of the interference signal data without performing measurement for the purpose of obtaining the interference signal data.

As described above, in the embodiment, the signal of interest can be extracted from the measurement data including the interference signal data without performing measurement for the purpose of obtaining the interference signal data. Therefore, since the number of measurement counts can be reduced to one, measurement time (i.e., inspection time) can be shortened compared with the conventional method, and a burden of the subject P can be reduced.

Additionally, in the embodiment, in order to extract a high quality signal of interest, the subject P is required to maintain the same posture during measurement, for example, for a few minutes. If the subject P moves during measurement, the measurement data may contain a noise component caused by the movement of the subject P and cannot be used. Shortening the measurement time by enabling the signal of interest to be extracted by one measurement leads to shortening a duration in which the subject P is forced to maintain the same posture. As a result, the high quality signal of interest can be stably measured.

Second Embodiment

Figure 10:
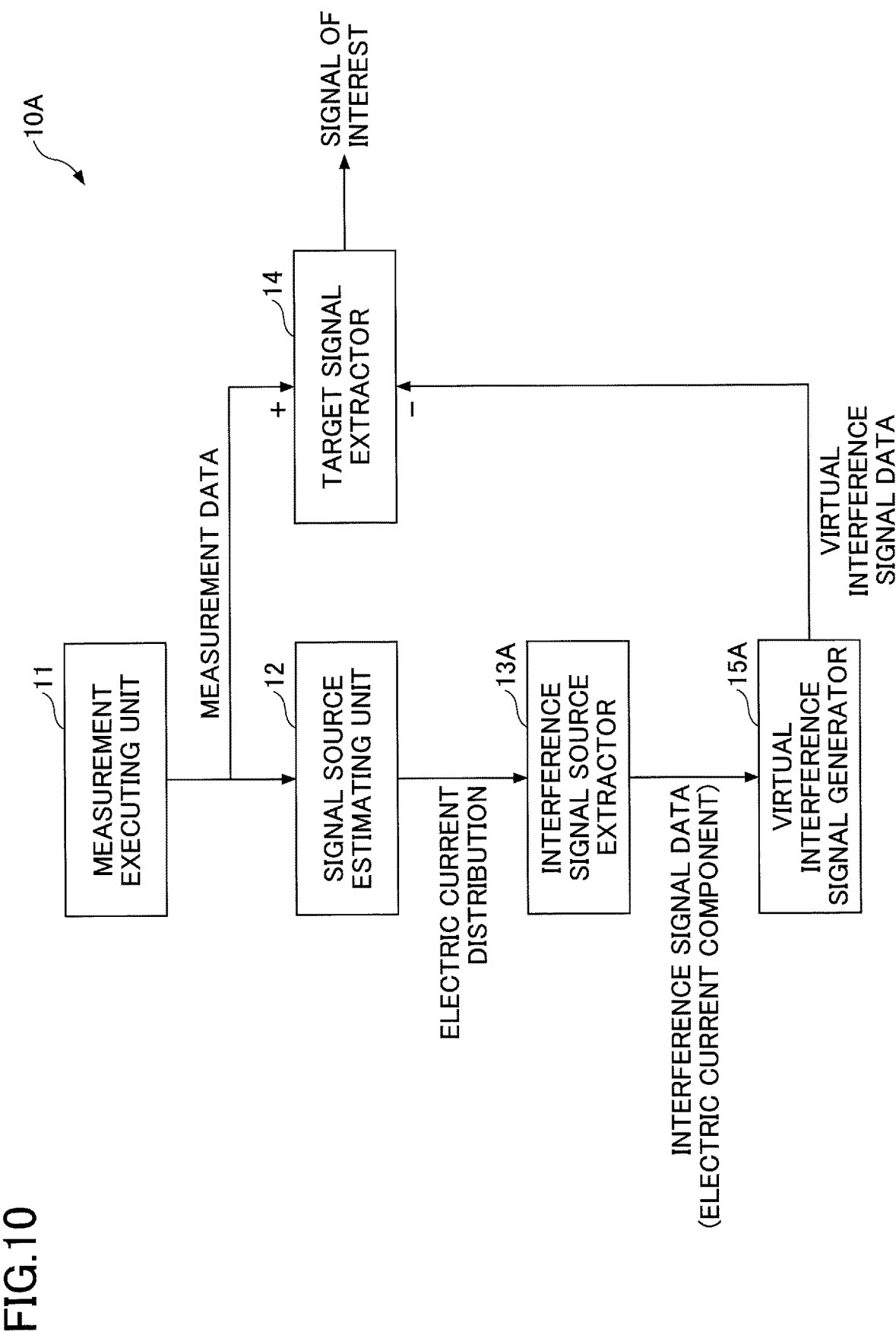
FIG. 10 is a block diagram illustrating an example of a signal processing apparatus according to a second embodiment.

FIG. 10 is a block diagram illustrating an example of the signal processing apparatus 10A according to a second embodiment. For the same elements as illustrated in FIG. 3, the same numerals are used and the detailed description is omitted. FIG. 10 also illustrates a functional block of the signal processing apparatus 10A. The signal processing apparatus 10A includes an interference signal source extractor 13A instead of the interference signal source extractor 13 of FIG. 3, and furthermore, a virtual interference signal generator 15A is added to the signal processing apparatus 10 of FIG. 3.

The interference signal source extractor 13A extracts the interference signal data (i.e., the electric current component) generated from the selected signal source of the interference signal and outputs the extracted interference signal data to the virtual interference signal generator 15A. The interference signal source extractor 13A has a function similar to the interference signal source extractor 13 illustrated in FIG. 3, except that the interference signal source extractor 13A does not have a function of generating the interference signal data (i.e., the magnetic field component) of the interference signal source extractor 13 illustrated in FIG. 3.

The virtual interference signal generator 15A calculates the virtual interference signal data (i.e., the magnetic field component) predicted to be obtained by the sensor array based on the interference signal data (i.e., the electric current component) extracted by the interference signal source extractor 13A. That is, the virtual interference signal generator 15A calculates a predicted value of the interference signal data that is the magnetic field data generated from the signal source of the interference signal and that is measured by the sensor array, based on the electric current distribution at the signal source of the interference signal. The process of extracting the signal of interest based on the measurement data obtained by the target signal extractor 14 and the virtual interference signal data is similar to the first embodiment.

Figure 11:
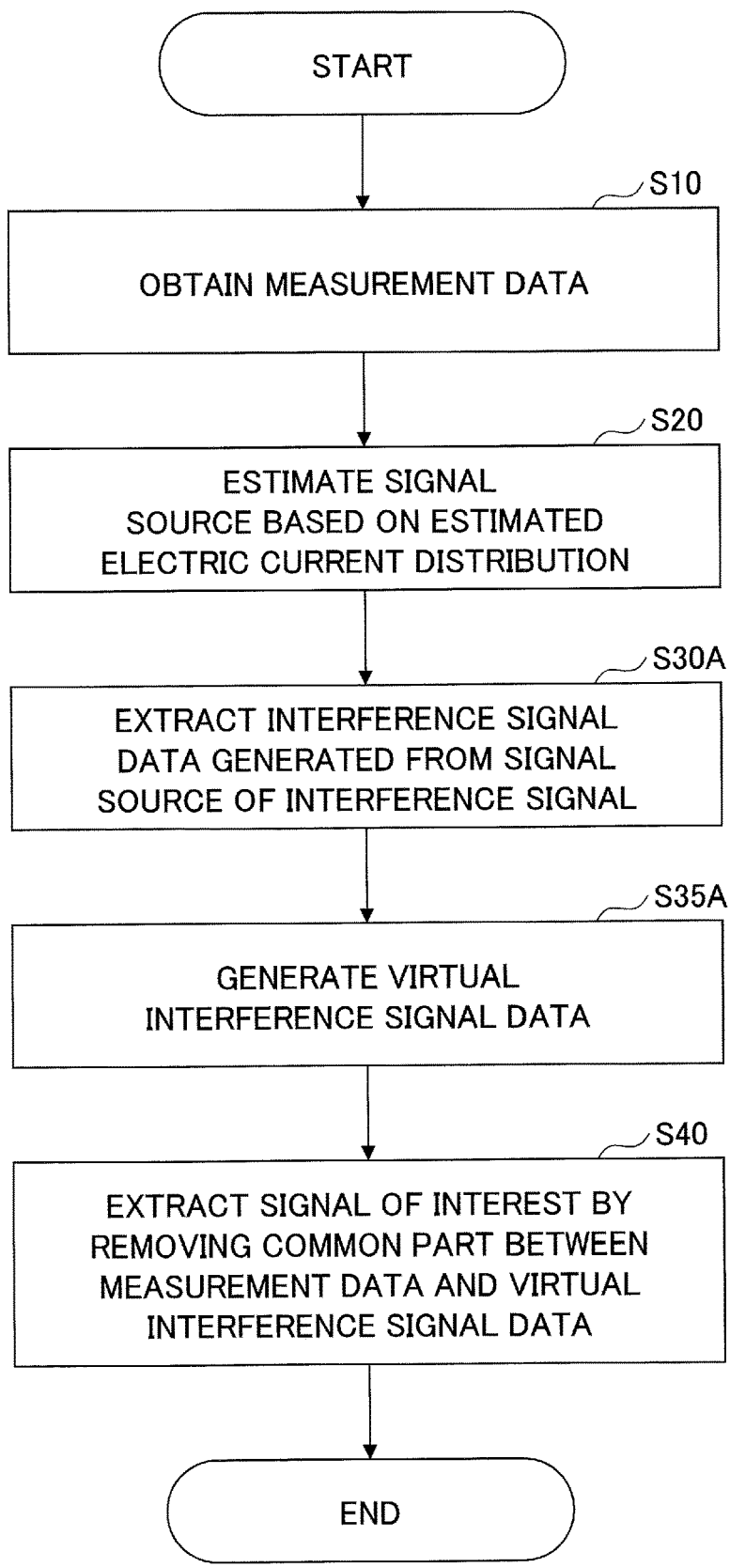
FIG. 11 is a flowchart illustrating an example of an operation of the signal processing apparatus of FIG. 10.

FIG. 11 is a flowchart illustrating an example of an operation of the signal processing apparatus 10A of FIG. 10. That is, FIG. 11 illustrates an example of a signal processing method by the signal processing apparatus 10A and a signal processing program that causes the signal processing apparatus 10A to perform the signal processing. For the same process as illustrated in FIG. 5, the detailed description is omitted.

In the process illustrated in FIG. 11, step S30A is performed instead of step S30 of FIG. 5, and step S35A is inserted between step S30A and step S40. The processing of step S10, step S20, and step S40 is the same as illustrated in FIG. 5.

In step S30A, the interference signal source extractor 13A selects the signal source in the area considered to be a generation source of the interference signal from among the signal sources estimated in step S20, and extracts the interference signal data (i.e., the electric current component). The interference signal source extractor 13A outputs the extracted interference signal data (i.e., the electric current component) to the virtual interference signal generator 15A.

Next, in step S35A, the virtual interference signal generator 15A calculates the virtual interference signal data (i.e., the magnetic field component) predicted to be obtained by the sensor array based on the interference signal data (i.e., the electric current component) and outputs the calculated virtual interference signal data to the target signal extractor 14. Subsequently, the same processing as in step S40 of FIG. 5 is performed, the signal of interest is extracted by removing a common part between the measurement data and the virtual interference signal data, and the process ends.

As described above, the second embodiment can obtain an effect similar to the first embodiment. In the second embodiment, the virtual interference signal data (i.e., the magnetic field component) calculated by the virtual interference signal generator 15A is output to the target signal extractor 14 so that the target signal extractor 14 can extract the signal of interest using the virtual interference signal data with high accuracy. As a result, the accuracy of the inspection can be further improved.

Third Embodiment

Figure 12:
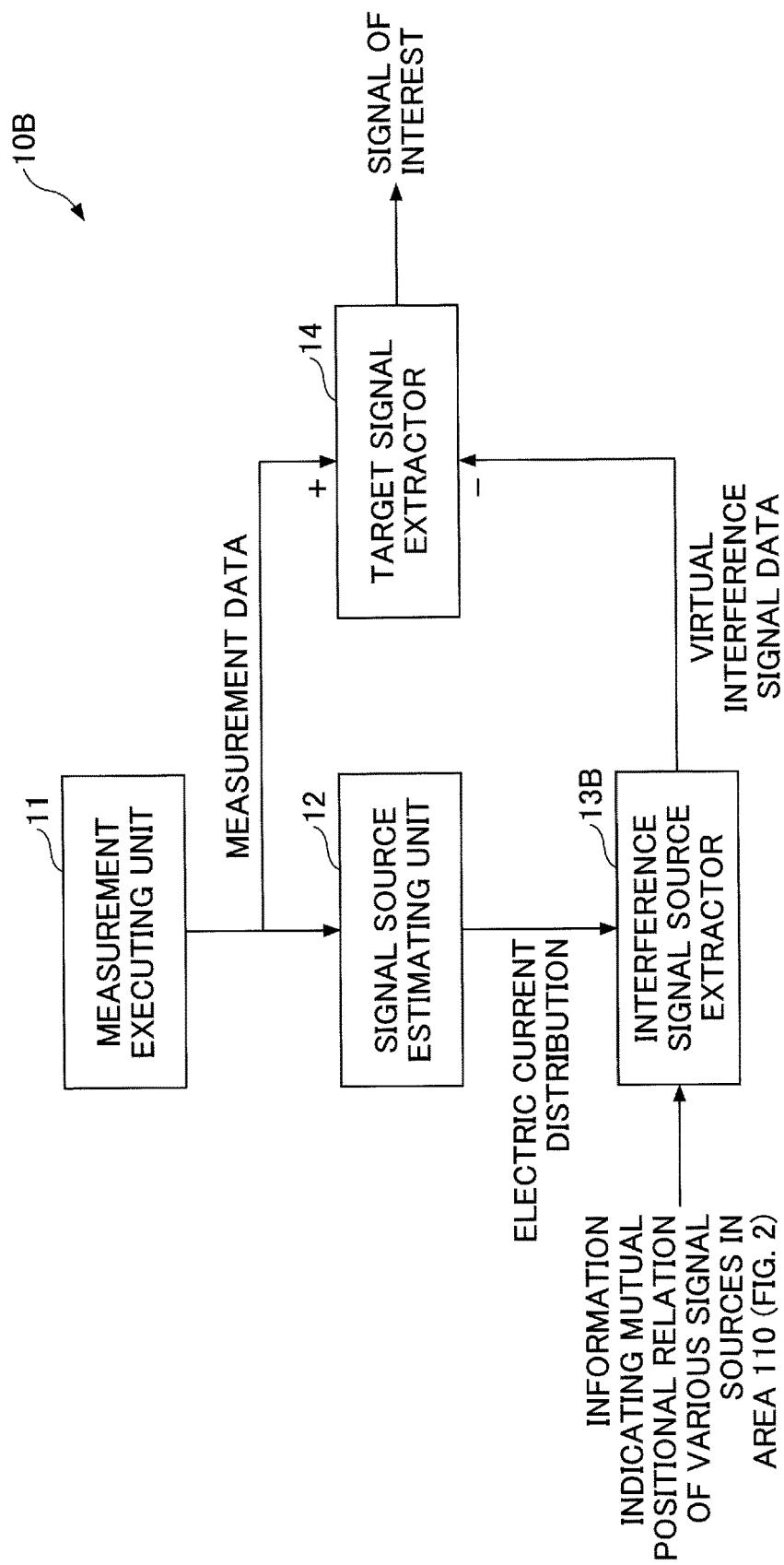
FIG. 12 is a block diagram illustrating an example of a signal processing apparatus according to a third embodiment.

FIG. 12 is a block diagram illustrating an example of the signal processing apparatus 10B according to a third embodiment. For the same elements as illustrated in FIG. 3, the same numerals are used and the detailed description is omitted. FIG. 12 also illustrates a functional block of the signal processing apparatus 10B. The signal processing apparatus 10B is similar to the signal processing apparatus 10 of FIG. 3 except that the signal processing apparatus 10B includes the interference signal source extractor 13B instead of the interference signal source extractor 13 of FIG. 3.

The interference signal source extractor 13B receives information indicating a mutual positional relation of various signal sources in the extraction target area 110 illustrated in FIG. 2 and selects an area having characteristics of the interference signal from among the signal sources estimated by the signal source estimating unit 12 as the signal source of the interference signal using the received information. Here, the information received by the interference signal source extractor 13B includes position information of the palm of the subject P that is the signal source of the signal of interest and position information of the electrode 106 that is the signal source of the artifact noise.

The interference signal source extractor 13B extracts the interference signal data (i.e., the electric current component) generated from the selected signal source of the interference signal and generates the virtual interference signal data (i.e., the magnetic field component) that is a predicted value of the magnetic field data generated from the signal source of the interference signal. The generated virtual interference signal data is output to the target signal extractor 14. By using information indicating the mutual positional relation of various signal sources, the accuracy of the virtual interference signal data (i.e., the electric current component and the magnetic field component) generated by the interference signal source extractor 13B can be improved.

As described above, the third embodiment can obtain an effect similar to the first embodiment. Furthermore, in the third embodiment, by using information indicating the mutual positional relation of the various signal sources, the accuracy of the interference signal data (i.e., the electric current component and the magnetic field component) can be improved. As a result, by increasing the extraction accuracy of the signal of interest by the target signal extractor 14, the accuracy of the inspection can be further improved.

Fourth Embodiment

Figure 13:
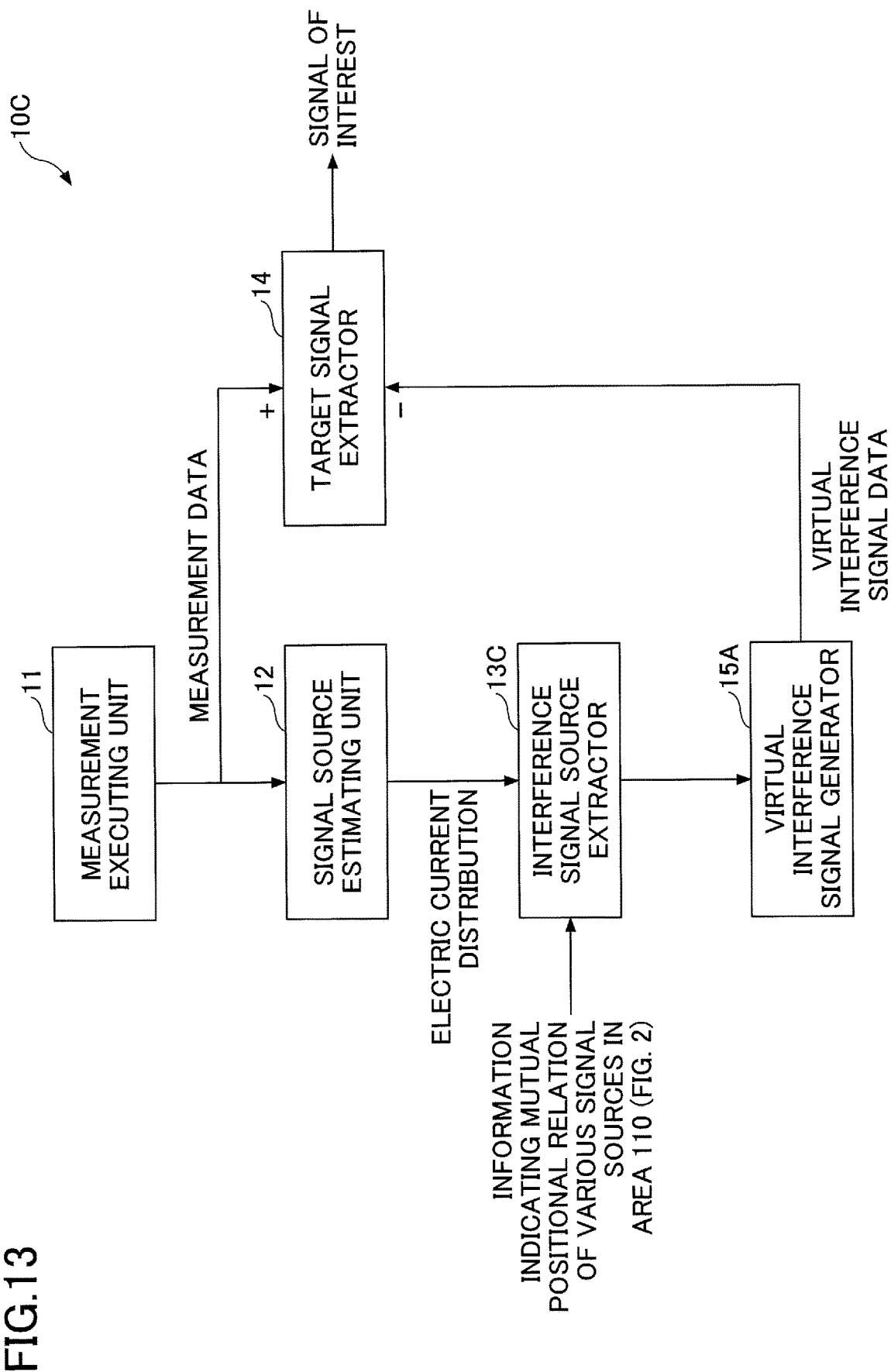
FIG. 13 is a block diagram illustrating an example of a signal processing apparatus according to a fourth embodiment.

FIG. 13 is a block diagram illustrating an example of a signal processing apparatus 10C according to a fourth embodiment. For the same elements as illustrated in FIG. 10, the same numerals are used and the detailed description is omitted. FIG. 13 also illustrates a functional block of the signal processing apparatus 10C. The signal processing apparatus 100 is similar to the signal processing apparatus 10A of FIG. 10 except that the signal processing apparatus 10C includes an interference signal source extractor 130 instead of the interference signal source extractor 13A of FIG. 10.

The interference signal source extractor 13C receives information indicating a mutual positional relation of various signal sources in the extraction target area 110 illustrated in FIG. 2 and selects an area having characteristics of the interference signal from among the signal sources estimated by the signal source estimating unit 12 as the signal source of the interference signal using the received information. The interference signal source extractor 130 extracts the interference signal data (i.e., the electric current component) generated from the selected signal source of the interference signal and outputs the extracted interference signal data to the virtual interference signal generator 15A.

The interference signal source extractor 13C can correctly select the signal source of the interference signal using information indicating the mutual positional relation of various signal sources and can accurately extract the interference signal data (i.e., the electric current component). As a result, the accuracy of the virtual interference signal data generated by the virtual interference signal generator 15A can be improved, and by increasing the extraction accuracy of the signal of interest, the accuracy of the inspection can be further improved.

As described above, the fourth embodiment can obtain an effect similar to the second embodiment. Furthermore, in the fourth embodiment, by using information indicating the mutual positional relationship of the various signal sources, the interference signal data (i.e., the electric current component) can be accurately extracted, and by increasing the extraction accuracy of the signal of interest, the accuracy of the inspection can be further improved.

In any one of embodiments described above, the target signal extractor 14 may extract the signal of interest by the SSP method (i.e., the signal subspace project method; Non-Patent Document 4) using the interference signal data or the virtual interference signal data with respect to input measurement data. The SSP method is a method for removing a component included in the interference signal data or the virtual interference signal data. When a data model of the interference signal follows a following equation (3), the signal of interest can be correctly extracted.

$$B_i = A + \varepsilon \quad (3)$$

In Eq. (3), A indicates the interference signal component, and $\varepsilon$ indicates white noise. Virtual interference signal data $B_i$ is data when only the interference signal component A is included in the virtual interference signal data $B_a$ obtained by Eq. (2).

Figure 14:
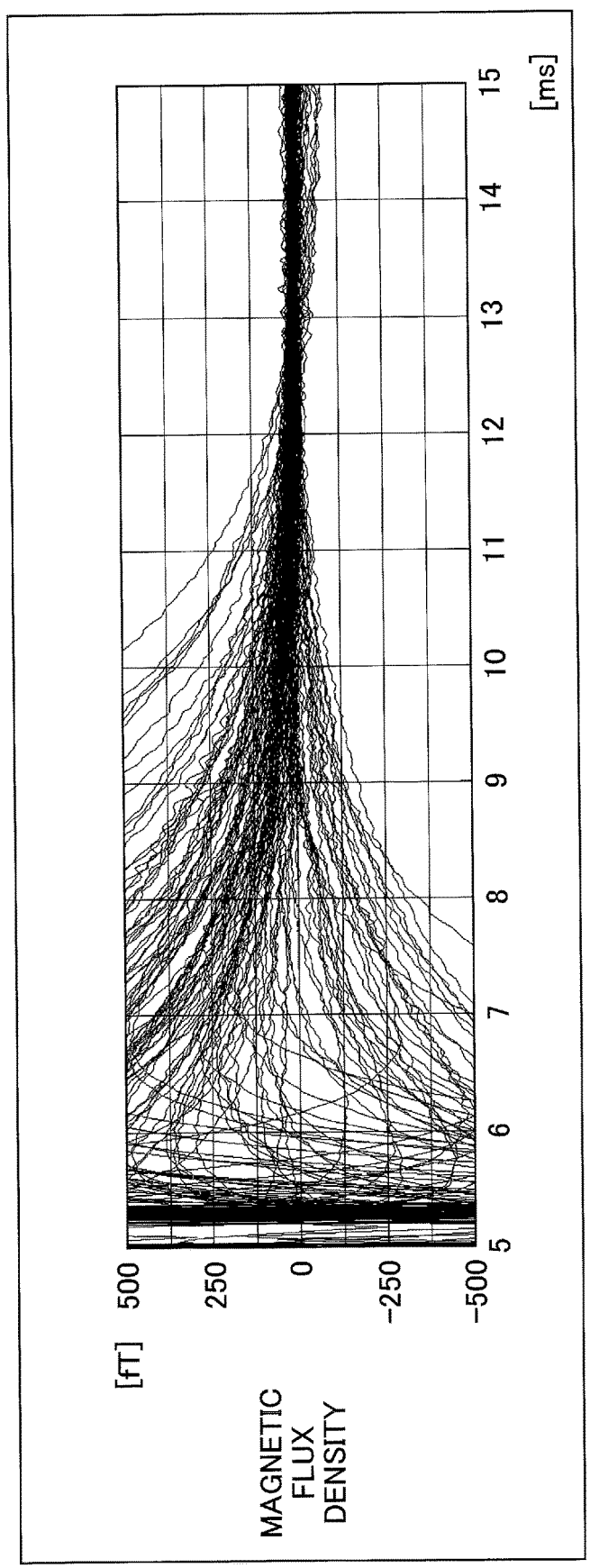
FIG. 14 is a drawing illustrating an example of measurement data obtained by measurement of the measurement executing unit illustrated in FIG. 3, FIG. 10, FIG. 12, or FIG. 13.
Figure 15:
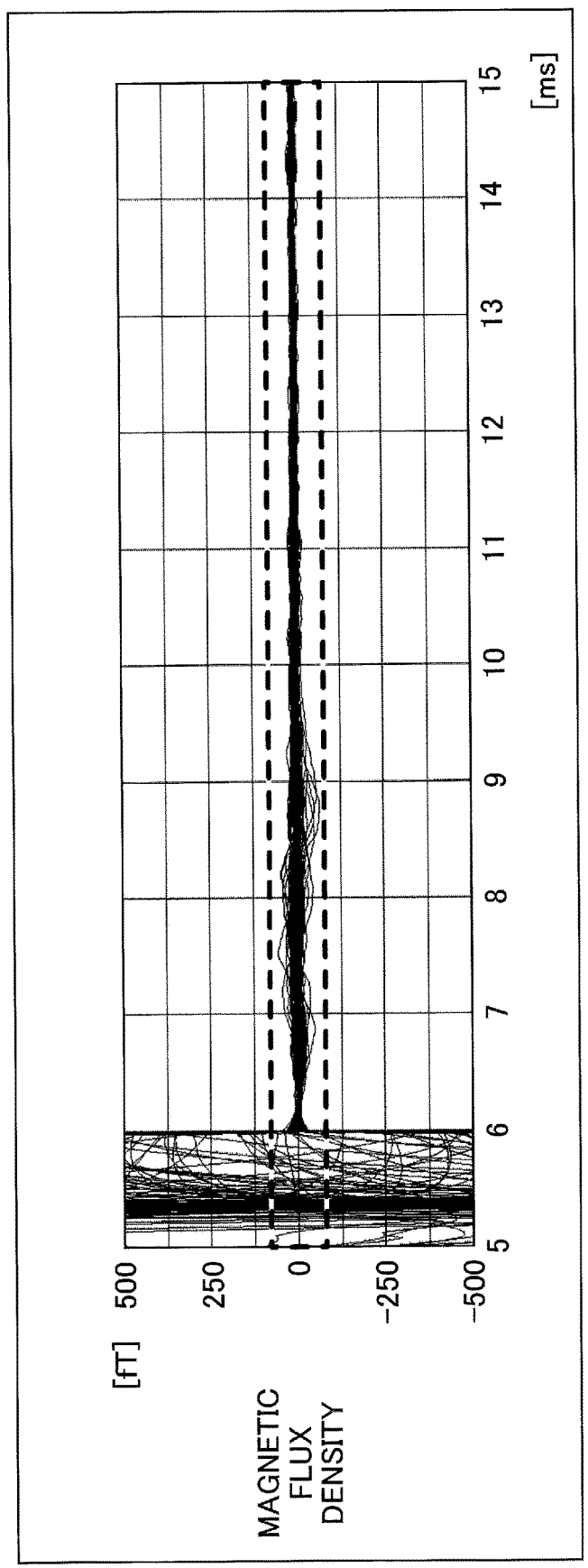
FIG. 15 is a drawing illustrating an example of a waveform of a signal of interest extracted by the target signal extractor illustrated in FIG. 3, FIG. 10, FIG. 12, or FIG. 13 using an SSP method.
Figure 16:
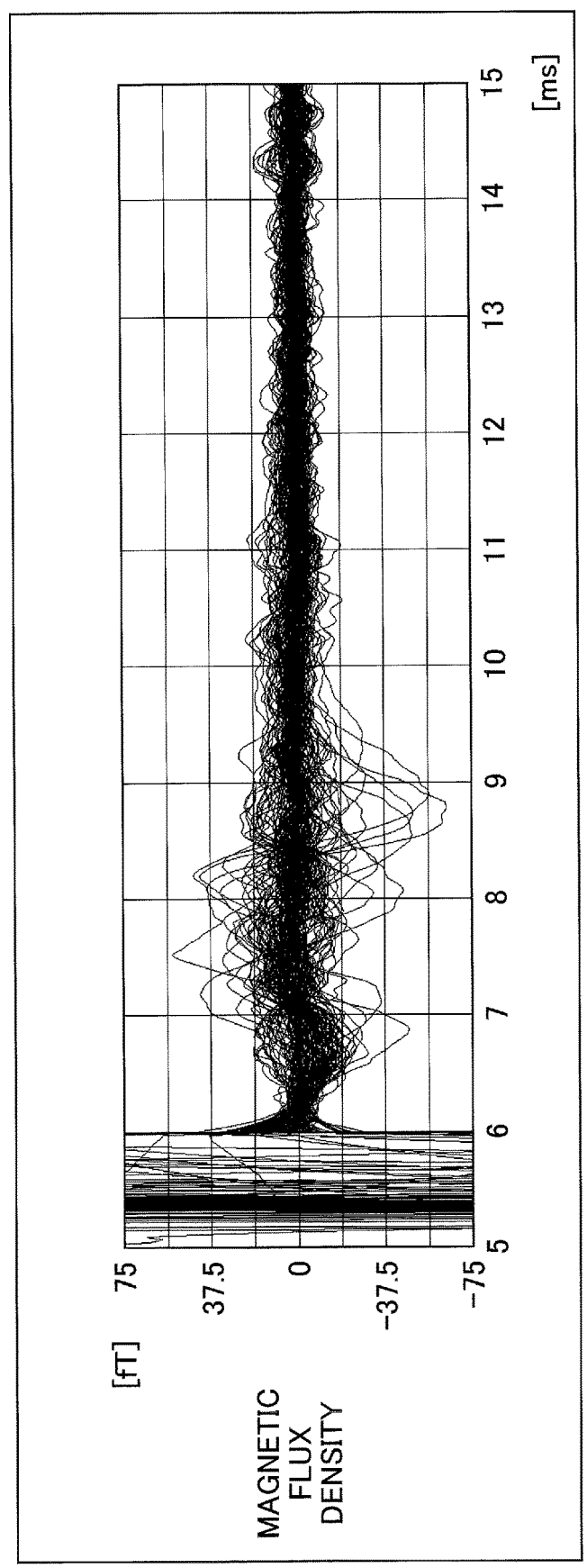
FIG. 16 is an enlarged view of the part inside the dashed frame of FIG. 15.

FIG. 14 to FIG. 16 illustrate an example of data when the signal of interest is extracted using the SSP method.

FIG. 14 is a drawing illustrating an example of the measurement data obtained by measurement of the measurement executing unit 11 illustrated in FIG. 3, FIG. 10, FIG. 12, or FIG. 13. In FIG. 14, as in FIG. 6, the interference signal generated by the electrical stimulation can be mainly observed, but a biosignal component (i.e., the signal of interest) is buried by the interference signal and cannot be observed.

FIG. 15 is a drawing illustrating an example of a waveform of the signal of interest extracted by the target signal extractor 14 illustrated in FIG. 3, FIG. 10, FIG. 12, or FIG. 13 using the SSP method. FIG. 16 is an enlarged view of a part inside the dashed frame of FIG. 15. In FIG. 15 and FIG. 16, the interference signal component is removed and the biosignal that is the signal of interest can be observed, as seen by comparing with FIG. 14.

In the embodiments described above, as illustrated in FIG. 2, a case in which the electrode 106 that is the signal source of the interference signal is outside of the measurement area 108 has been described. However, the signal source of the interference signal may be in the measurement area 108. In this case, the signal of interest can also be extracted by removing a common part between the measurement data and the virtual interference signal data.

This is because the signal source estimating unit 12 can estimate a position of the signal source even when the signal source of the interference signal is in the measurement area 108 as long as the electric current distribution is obtained, because the signal source estimating unit 12 estimates a position of the signal source of the interference signal such as the electrode 106 based on the electric current distribution in the extraction target area 110. Therefore, the signal source of the interference signal data can be selected by the interference signal source extractor 13, 13A, 13B, or 13C, the interference signal data can be extracted, and the signal of interest can be extracted by the target signal extractor 14.

In the embodiments described above, a method for extracting the signal of interest by removing the interference signal data caused by the artifact noise from the measurement data is described. However, the interference signal data to be removed from the measurement data may be biomagnetic field data other than the biomagnetic field data generated at the body part to be measured in response to the stimulation (i.e., biomagnetic field noise). For example, biomagnetic field data generated at a part other than the body part to be measured includes magnetic field data generated by a muscle activity. In the embodiments described above, since the position of the electrode 106 or the like, which is the signal source of the interference signal, is estimated based on the electric current distribution in the extraction target area 110, both artifact noise and biomagnetic field noise can be removed by one measurement for example.

(Application Example)

An example of applying the method of the disclosure described above will be described below. Here, an example of performing the biomagnetic field measurement will be described by assuming that the body part to be measured is the palm, but the body part is not limited to this. The method of the disclosure can be also applied to other body parts.

Figure 17:
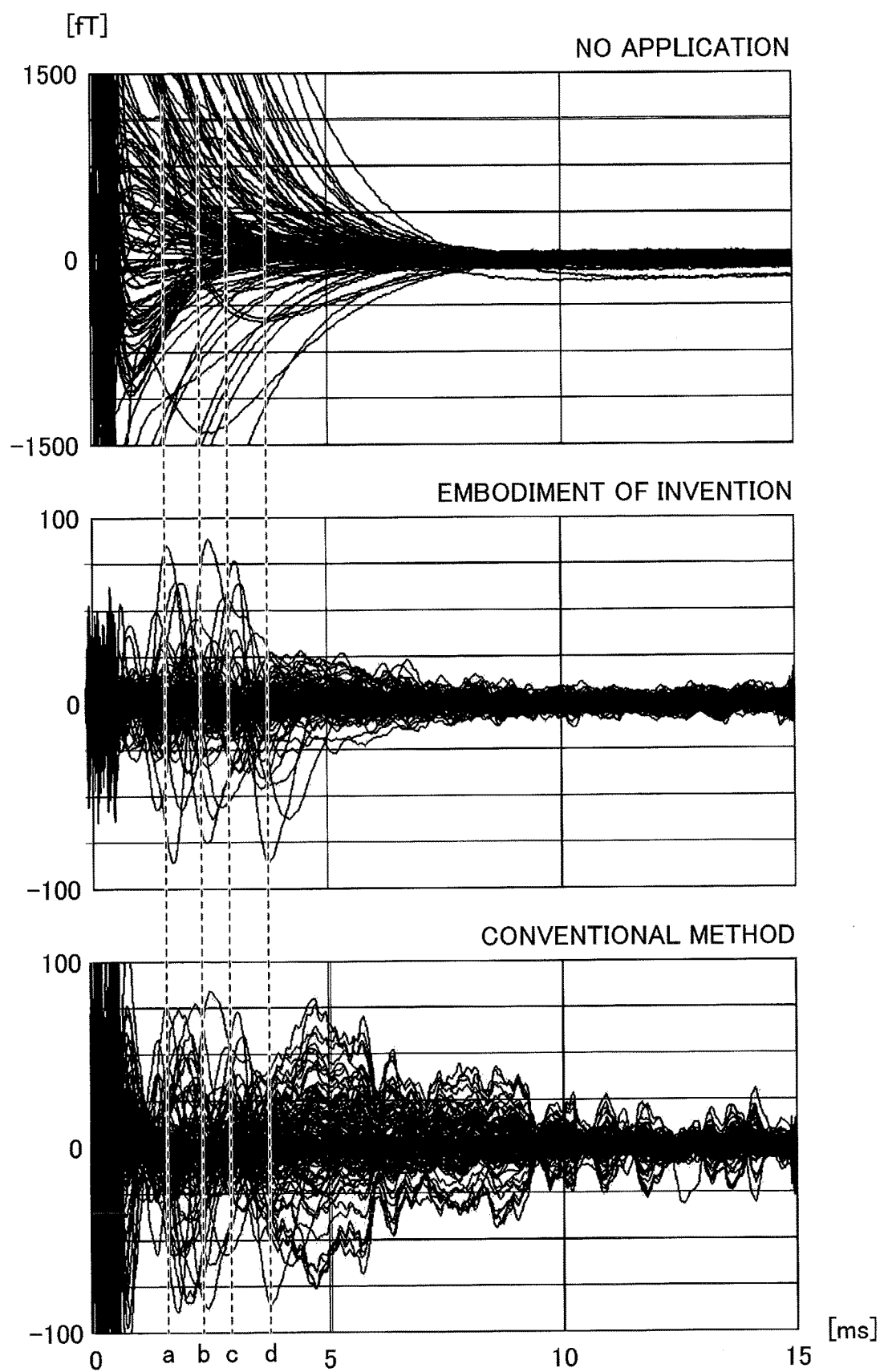
FIG. 17 is a drawing illustrating examples of a case in which an artifact removal is not applied, a case in which an embodiment is applied, and a case in which a conventional method is applied, with respect to magnetic field data measured on a palm.

As illustrated in FIG. 2, the palm of the subject was placed on the apparatus, the electrical stimulation is given from the stimulating electrode 106, and the magnetic field generated by an induced nerve activity electric current was measured multiple times to obtain the magnetic field data with white noise reduced by adding and averaging. Magnetic field data without applying artifact removal to the obtained magnetic field data, magnetic field data generated by applying the embodiment of the invention to the obtained magnetic field data, and magnetic field data generated by applying the conventional method to the obtained magnetic field data, are illustrated. Output waveforms of the magnetic field from all sensors are illustrated in FIG. 17 as time on the horizontal axis and magnetic field strength on the vertical axis.

In the magnetic field data without applying artifact removal, stimulation artifacts remain and the biomagnetic field signal cannot be observed. With respect to this, in the magnetic field data generated by applying the embodiment of the invention, the biological field signal can be observed before a latency of 5 ms. In the magnetic field data generated by applying the conventional method, the biomagnetic field signal is observed before a latency of 5 ms, but artifacts that could not be removed remain around a latency of 5 ms, and a transferred noise component can be observed at a later latency.

Figure 18:
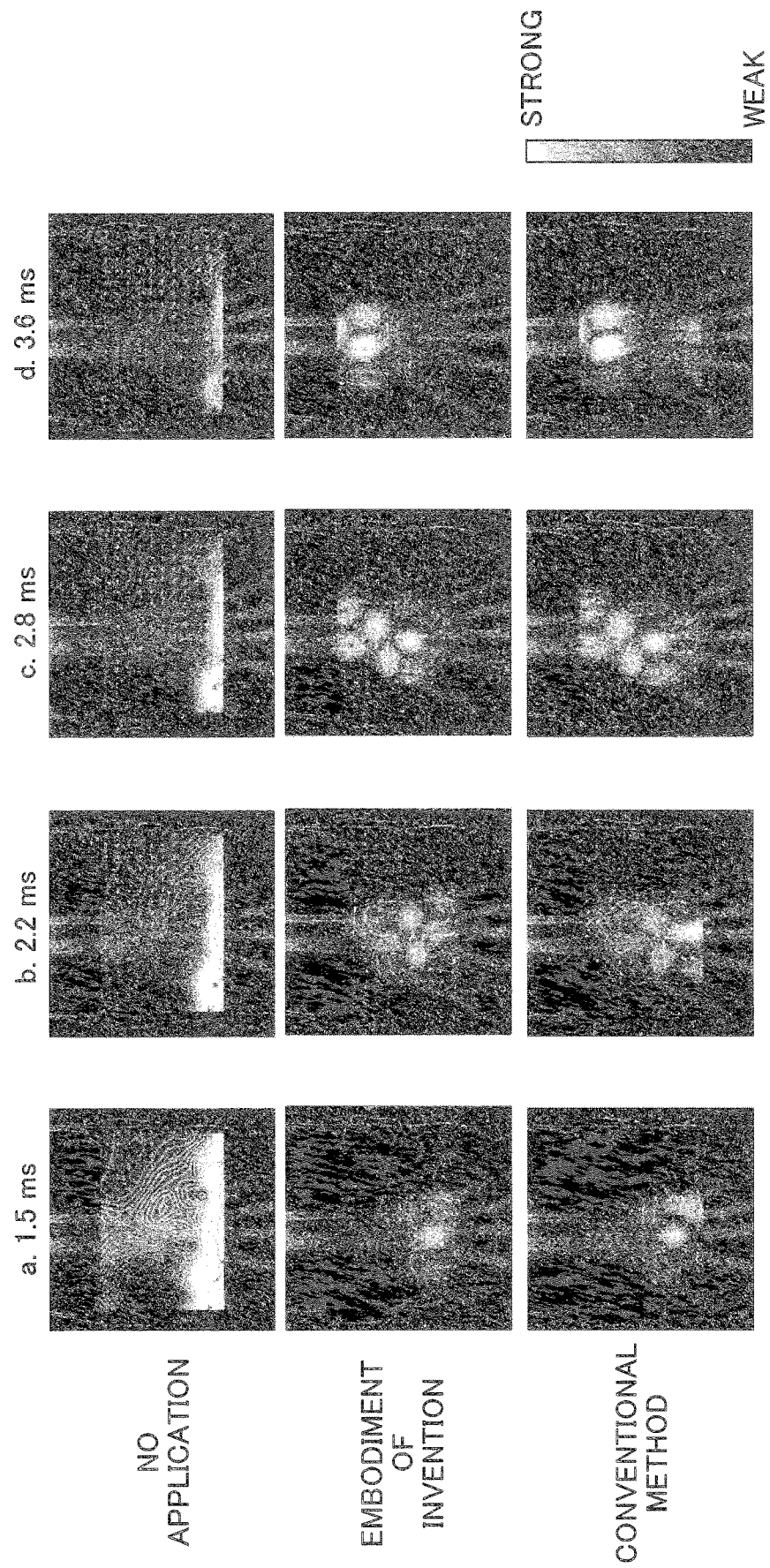
FIG. 18 is a drawing illustrating an example of visualizing a nerve activity electric current with respect to the magnetic data illustrated in FIG. 17.

A RENS filter (Non-Patent Document 5), which is one of a spatial filter method, was applied to the magnetic field data without applying artifact removal, the magnetic field data after applying the embodiment of the invention, and the magnetic field data after applying the conventional method, at latency time illustrated in dashed lines a, b, c, and d in FIG. 18, to visualize a nerve activity electric current. The visualized nerve activity electric current is placed on the form information using the method of Patent Document 3 and is illustrated in FIG. 18.

FIG. 18 illustrates the intensity of an electric current as the brightness in the contour diagram, and illustrates that as a contour line approaches white, a stronger electric current exists. Additionally, a direction of the electric current at each position to be measured is indicated by a gray arrow.

The nerve activity electric current is composed of a preceding axon electric current component directed in a conduction direction from depolarization along an axon, a succeeding axon electric current component directed in a direction opposite to a conduction direction from depolarization along an axon, and a volume electric current component that flows outside of a neural axon to compensate for the two electric current components in the axon. Each electric current component is conducted with maintaining a positional relation.

When the electric current distribution visualized from the data to which the artifact removal was not applied is checked, only a strong electric current exists at the distal side of the hand and at the outside of the hand, and no nerve activity electric current component is observed.

When the electric current distribution visualized from the data after applying the embodiment of the invention is checked, it can be observed that the nerve activity electric current was transmitted from the middle finger to which the stimulation was applied toward a proximal side.

When the electric current distribution visualized from the data after applying the conventional method is checked, it can be observed that the nerve activity electric current was transmitted from the middle finger to which the stimulation was applied toward a proximal side. However, when the electric current distribution visualized from the magnetic field data at a latency of 3.6 ms on the line d is checked, an electric current component other than the nerve activity electric current is observed at the distal side of the hand. This is considered to be an electric current visualized from the artifact component that could not be removed.

Additionally, since the electric current distribution obtained by the spatial filter method has position information and electric current intensity for each time point, it is possible to obtain an electric current waveform at a given point.

Figure 19:
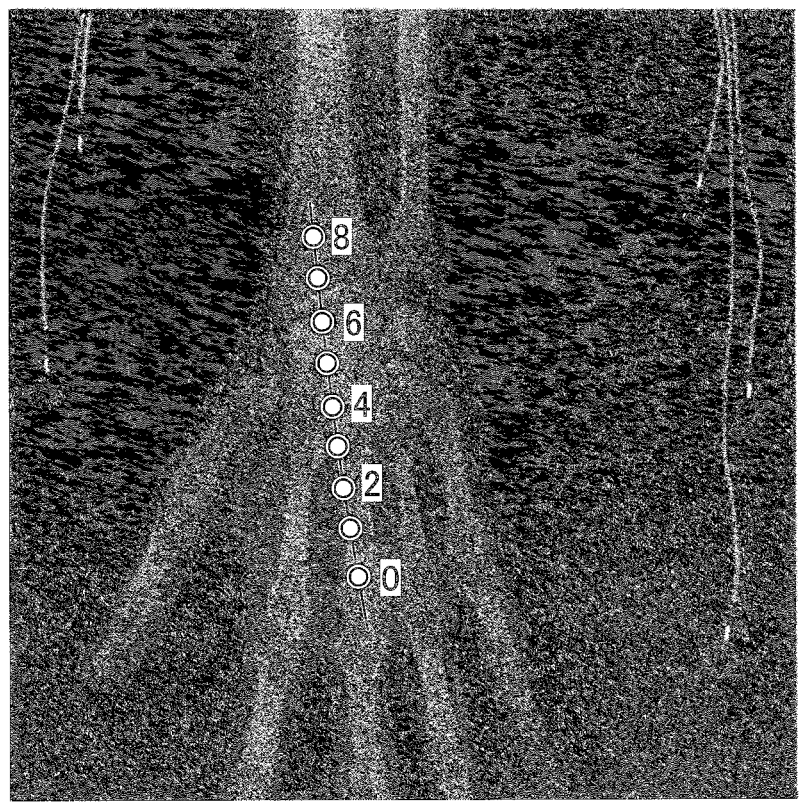
FIG. 19 is a drawing illustrating an example of setting current waveform obtaining points at equal intervals on a conduction path of an axon electric current component.
Figure 20:
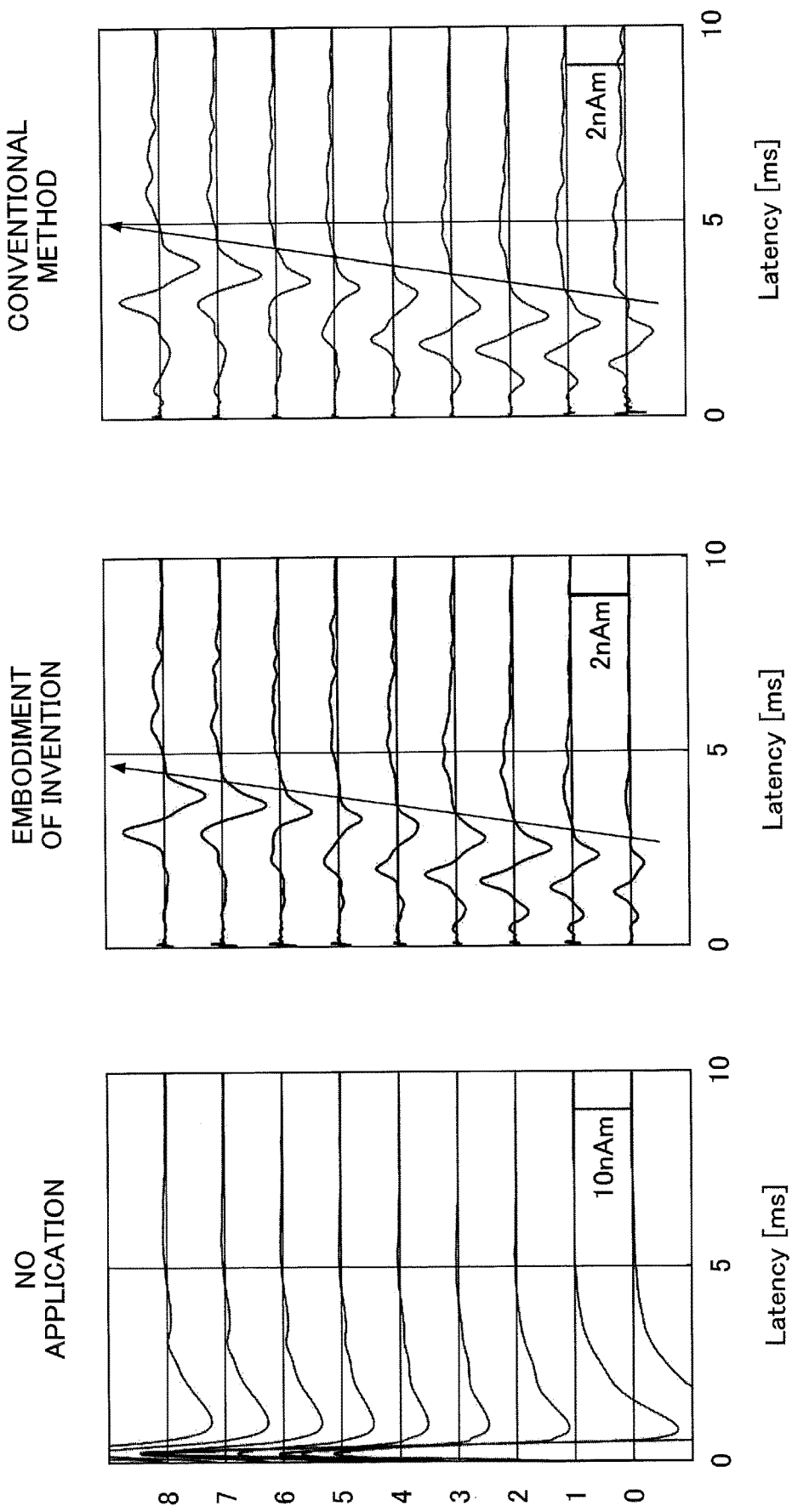
FIG. 20 is a drawing illustrating an example of a current waveform obtained at each current waveform obtaining point of FIG. 19.

Multiple electric current waveform obtaining points were set at equal intervals on a conduction path of the axon electric current component as illustrated in FIG. 19. An electric current waveform at each point was obtained and was arranged as illustrated in FIG. 20. An electric current waveform obtained from the data to which the embodiment of the invention was applied and an electric current waveform obtained from the data to which the conventional method was applied indicate that a peak latency was shifted backward on the time axis as the electric current waveform obtaining point was more proximal and a conduction of nerve activity could be also obtained as a waveform. With respect to this, an electric current waveform obtained from the data to which artifact removal was not applied indicate that a waveform of the nerve activity electric current was buried by the artifact electric current waveform, and a conduction of the nerve activity could not be evaluated as a waveform.

By applying the embodiment of the invention, the magnetic field data in which artifacts are removed was obtained in half the time of the conventional method and it was confirmed that nerve activity could be evaluated as a waveform comparable to the waveform of the conventional method.

Figure 21:
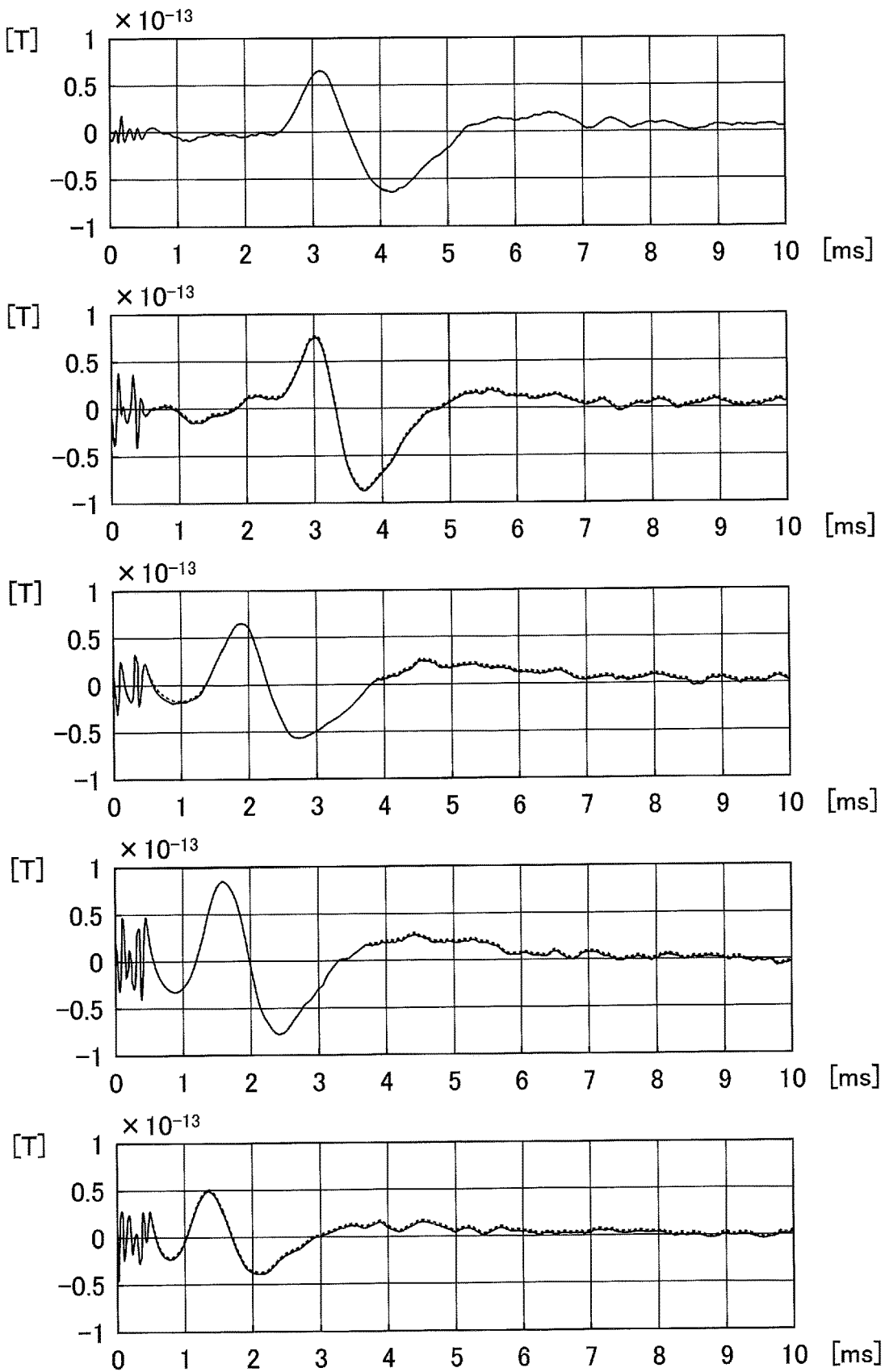
FIG. 21 is a drawing illustrating a waveform of a magnetic field of a sensor output that particularly clearly captures each biomagnetic field signal.

In the description above, an embodiment in which a magnetic field component is used as the interference signal data to the target signal extractor and an embodiment in which an electric current component is used are described. FIG. 21 illustrates output waveforms of the five sensors in which a biosignal component appeared well (a waveform shape was clearly observed) among the magnetic field data obtained by applying each of the methods of using the magnetic field component and using the electric current component as the interference signal data to the magnetic field data obtained by the method of giving the electrical stimulation from the stimulating electrode 106 to the palm of the subject placed on the apparatus as illustrated in FIG. 2, measuring the magnetic field generated by an induced nerve activity electric current multiple times, and adding and averaging the measured results to reduce white noise. The waveform obtained by applying the method of using the magnetic field component as the interference signal data is illustrated as a black solid line, and the waveform obtained by applying the method of using the electric current component as the interference signal data is illustrated as a black dashed line. It can be confirmed that the effect of either method is comparable. Here, the unit of the horizontal axis of each graph is ms.

According to the embodiment of the present invention, it is possible to extract the magnetic field data of interest by removing the interference magnetic field data from the measurement data of the magnetic field and shorten the measurement time.

Although the invention has been described above in accordance with the embodiments, the invention is not limited to the requirements described in the embodiments. In these points, alterations can be made without departing from the spirit and scope of the invention, and can be suitably determined according to its application.

What is claimed is:

1. A signal processing apparatus comprising:
a memory; and
a processor coupled to the memory and configured to perform a process including
obtaining measurement data including a signal of interest and an interference signal generated in proximity to a first signal source of the signal of interest;
estimating a second signal source of the interference signal in an extraction target area including the first signal source of the signal of interest and the second signal source of the interference signal based on the measurement data;
extracting interference signal data generated from the second signal source of the interference signal based on a result of the estimating the second signal source;
generating virtual interference signal data from the interference signal data, and
extracting the signal of interest by removing a common part between the measurement data and the virtual interference signal data,
wherein the virtual interference signal data is generated based on an electric current component of the interference signal data, and
wherein the process includes visualizing an electric current of biological activity based on the extracted signal of interest and the visualizing of the electric current of the biological activity includes displaying a region where the electric current of the biological activity is present and changing a color of the region in accordance with an intensity of the electric current of the biological activity.

2. The signal processing apparatus as claimed in claim 1,
wherein the measurement data is magnetic field data,
wherein the estimating the second signal source includes obtaining an electric cuneiiit distribution in the extraction target area and estimating the second signal source of the interference signal based on the electric current distribution, and
wherein the extracting interference signal data includes extracting a magnetic field component of the interference signal data generated from the second signal source of the interference signal estimated based on the electric current distribution.

3. The signal processing apparatus as claimed in claim 1,
wherein the virtual interference signal data is indicated by a magnetic field component based on the electric current component of the interference signal data, and
wherein the signal of interest is extracted from the measurement data that is magnetic field data and the virtual interference signal data.

4. The signal processing apparatus as claimed in claim 1,
wherein the extracting interference signal data includes receiving information indicating a position relation between the first signal source of the signal of interest and the second signal source of the interference signal and extracting the interference signal data based on the information.

5. The signal processing apparatus as claimed in claim 1, wherein the signal of interest is extracted using a signal subspace projection method.

6. A signal processing apparatus comprising:
a memory; and
a processor coupled to the memory and configured to perform a process including
obtaining measurement data including a signal of interest and an interference signal generated in proximity to a first signal source of the signal of interest;
estimating a second signal source of the interference signal in an extraction target area including the first signal source of the signal of interest and the second signal source of the interference signal based on the measurement data;
extracting interference signal data generated from the second signal source of the interference signal based on a result of the estimating the second signal source: and
extracting the signal of interest by removing a common part between the measurement. data and the interference signal data,
wherein the measurement data. includes the signal of interest generated by a nerve-induced magnetic field generated by nerve activity of a subject induced by an electrical stimulation that the subject receives and the interference signal generated by an interference magnetic field generated by the electrical stimulation,
wherein the first signal source of the signal of interest is a part of the subject to be measured,
wherein the second signal source of the interference signal is an electrode attached to the subject for giving the electrical stimulation to the subject, and
wherein the process includes visualizing an electric current of the nerve activity based on the extracted signal of interest and the visualizing of the electric current of the nerve activity includes displaying a region where the electric current of the nerve activity is present and changing a color of the region in accordance with an intensity of the electric current of the nerve activity.

7. The signal processing apparatus as claimed in claim 6,
wherein the measurement data includes the signal of interest generated by the nerve-induced magnetic field generated by the nerve activity of a palm of the subject induced by the electrical stimulation that a finger receives and the interference signal generated by the interference magnetic field generated by the electrical stimulation.

8. The signal processing apparatus as claimed in claim 6, comprising a plurality of magnetic sensors disposed at positions facing the part of the subject to be measured.

9. A signal processing apparatus comprising:
a memory; and
a processor coupled to the memory and configured to perform a. process including
obtaining measurement data including a signal of interest and an interference signal generated in proximity to a first signal source of the signal of interest;
estimating a second signal source of the interference signal in an extraction target area including the first signal source of the signal of interest and the second signal source of the interference signal based on the measurement data;
extracting, interference signal data generated from the second signal source of the interference signal based on a result of the estimating the second signal source; and
extracting the signal of interest by removing a common part between the measurement data and the interference signal data, wherein the measurement data includes the signal of interest generated by a nerve-induced magnetic field generated by nerve activity of a subject induced by an electrical stimulation that the subject receives and the interference signal generated by an interference magnetic field generated by the electrical stimulation, wherein the first signal source of the signal of interest is a part of the subject to be measured, wherein the second signal source of the interference signal is a part that is other than the part of the subject to be measured and that generates the interference magnetic field by the nerve activity induced by the electrical stimulation, and wherein the process includes visualizing an electric current of the nerve activity based on the extracted signal of interest and the visualizing of the electric current of the nerve activity includes displaying a region where the electric current of the nerve activity is present and changing a color of the region in accordance with an intensity of the electric. current of the nerve activity.

10. A signal processing method by a signal processing apparatus including a measurement executing unit configured to obtain measurement data including a signal of interest and an interference signal generated in proximity to a first signal source of the signal of interest, the signal processing method comprising:

estimating a second signal source of the interference signal in an extraction target area including the first signal source of the signal of interest and the second signal source of the interference signal based on the measurement data;

extracting interference signal data generated from the second signal source of the interference signal based on a result of the estimating the second signal source;

generating virtual interference signal data from the interference signal data, and extracting the signal of interest by removing a common part between the measurement data and the virtual interference signal data, wherein the virtual interference signal data is generated based on an electric currentcomponent of the interference signal data, and wherein the signal processing method finther comprising visualizing an electric current of biological activity based on the extracted signal of interest and the visualizing of the electric current of the biological activity includes displaying a region where the electric current of the biological activity is present and changing a color of the region in accordance with an intensity of the electric current of the biological activity.

11. The signal processing method as claimed in claim 10,
wherein the measurement data is magnetic field data,
wherein the estimating the second signal source includes obtaining electric current distribution in the extraction target area and estimating the second signal source of the interference signal based on the electric current distribution, and
wherein the extracting interference signal data includes extracting an electric current component of the interference signal data generated from the estimated second signal source of the interference signal regarded as a magnetic field component.

12. The signal processing method as claimed in claim 10,
wherein the generating virtual interference signal data includes generating the virtual interference signal data indicated by a magnetic field component based on the electric current component of the interference signal data, and
wherein the extracting the signal of interest includes extracting the signal of interest from the measurement data that is magnetic field data and the virtual interference signal data.

13. A non-transitory computer-readable storage medium having stored therein a signal processing program for causing a signal processing apparatus to execute signal processing, the signal processing apparatus including a measurement executing unit configured to obtain measurement data including a signal of interest and an interference signal generated in proximity to a first signal source of the signal of interest, and the signal processing comprising:

estimating a second signal source of the interference signal in an extraction target area including the first signal source of the signal of interest and the second signal source of the interference signal based on the measurement data;

extracting interference signal data generated from the second signal source of the interference signal based on a result of the estimating the second signal source;

generating virtual interference signal data from the interference signal data, and extracting the signal of interest by removing a common part between the measurement data and the virtual interference signal data, wherein the virtual interference simal data is generated based on an electric current component of the interference signal data, and wherein the signal processing further comprising visualizing an electric current of biological activity based on the extracted signal of interest and the visualizing of the electric current of the biological activity includes displaying a region where the electric current of the biological activity is present and changing a color of the region in accordance with an intensity of the electric current of the biological activity.

14. The non-transitory computer-readable storage medium as claimed in claim 13,
wherein the measurement data is magnetic field data,
wherein the estimating the second signal source includes obtaining an electric cuirent distribution in the extraction target area and estimating the second signal source of the interference signal based on the electric current distribution, and
wherein the extracting interference signal data includes extracting an electric current component of the interference signal data generated from the estimated second signal source of the interference signal regarded as a magnetic field component.

15. The non-transitory computer-readable storage medium as claimed in claim 13,
wherein the generating virtual interference signal data includes generating the virtual interference signal data indicated by a magnetic field component based on the electric current component of the interference signal data, and
wherein the extracting the signal of interest includes extracting the signal of interest from the measurement data that is magnetic field data and the virtual interference sinal data.

* * * * *